US011521712B2

(12) United States Patent
Fan et al.

(10) Patent No.: US 11,521,712 B2
(45) Date of Patent: Dec. 6, 2022

(54) COMPUTATIONAL METHOD FOR CLASSIFYING AND PREDICTING LIGAND DOCKING CONFORMATIONS

(71) Applicant: ACCUTAR BIOTECHNOLOGY INC., Brooklyn, NY (US)

(72) Inventors: Jie Fan, New York, NY (US); Ke Liu, Shanghai (CN); Sun Xiangyan, Shanghai (CN)

(73) Assignee: Accutar Biotechnology Inc., Brooklyn, NY (US)

(*) Notice: Subject to any disclaimer, the term of this patent is extended or adjusted under 35 U.S.C. 154(b) by 1238 days.

(21) Appl. No.: 15/984,129

(22) Filed: May 18, 2018

(65) Prior Publication Data
US 2018/0341754 A1 Nov. 29, 2018

Related U.S. Application Data

(60) Provisional application No. 62/508,853, filed on May 19, 2017, provisional application No. 62/560,738, filed on Sep. 20, 2017.

(51) Int. Cl.
G01N 33/48 (2006.01)
G01N 33/50 (2006.01)
(Continued)

(52) U.S. Cl.
CPC .......... G16C 20/50 (2019.02); G06N 3/0454 (2013.01); G06N 3/08 (2013.01); G06N 3/084 (2013.01);
(Continued)

(58) Field of Classification Search
CPC ........ G16C 20/50; G16C 10/00; G16C 20/70; G16C 20/80; G16C 20/64; G06N 3/0454;
(Continued)

(56) References Cited

U.S. PATENT DOCUMENTS

2002/0099506 A1 7/2002 Floriano et al.
2006/0041414 A1 2/2006 Ho
(Continued)

FOREIGN PATENT DOCUMENTS

WO WO 2017/062382 A1 4/2017
WO WO-2017155840 A1 * 9/2017 ......... G01N 33/6803

OTHER PUBLICATIONS

Allen et al. Dock 6: Impact of new features and current docking performance. Journal of Computational Chemistry. vol. 36, pp. 1132-1156. (Year: 2015).*
(Continued)

Primary Examiner — Russell S Negin
(74) Attorney, Agent, or Firm — Finnegan, Henderson, Farabow, Garrett & & Dunner LLP

(57) ABSTRACT

A computer-implemented method for predicting a conformation of a ligand docked into a protein is disclosed. According to some embodiments, the method may include determining one or more poses of the ligand in the protein, the poses being representative conformations of the ligand. The method may also include determining, using a neural network, energy scores of the poses. The method may further include determining a proper conformation for the docked ligand based on the energy scores.

24 Claims, 17 Drawing Sheets

Exemplary Overall Neural Network Architecture

(51) Int. Cl.
| | |
|---|---|
| G16C 20/50 | (2019.01) |
| G06N 5/04 | (2006.01) |
| G06N 3/08 | (2006.01) |
| G16C 10/00 | (2019.01) |
| G16C 20/70 | (2019.01) |
| G16C 20/80 | (2019.01) |
| G06N 5/00 | (2006.01) |
| G06N 3/04 | (2006.01) |
| G16B 15/00 | (2019.01) |
| G16C 20/64 | (2019.01) |
| G16B 15/30 | (2019.01) |

(52) U.S. Cl.
CPC .............. G06N 5/003 (2013.01); G06N 5/046 (2013.01); G16B 15/00 (2019.02); G16C 10/00 (2019.02); G16C 20/70 (2019.02); G16C 20/80 (2019.02); G16B 15/30 (2019.02); G16C 20/64 (2019.02)

(58) Field of Classification Search
CPC .......... G06N 3/08; G06N 3/084; G06N 5/003; G06N 5/046; G16B 15/00; G16B 15/30
See application file for complete search history.

(56) References Cited

U.S. PATENT DOCUMENTS

| | | | |
|---|---|---|---|
| 2007/0134662 A1 | 6/2007 | Singh et al. | |
| 2007/0192037 A1* | 8/2007 | Jojic | G16B 15/20 702/19 |
| 2011/0112818 A1 | 5/2011 | Goddard, III et al. | |
| 2013/0330335 A1 | 12/2013 | Bremel et al. | |
| 2015/0134315 A1 | 5/2015 | Sarmiento et al. | |
| 2016/0132631 A1* | 5/2016 | Bremel | G16B 5/00 703/2 |
| 2017/0032078 A1 | 2/2017 | Stelzer et al. | |

OTHER PUBLICATIONS

Ballester et al. A machine learning approach to predicting protein-ligand binding affinity with applications to molecular docking. Bioinformatics, vol. 26, pp. 1169-1175. (Year: 2010).*

Duvenaud et al. Convolutional networks on graphs for learning molecular fingerprints. In Advances in Neural Information Processing Systems, pp. 2224-2232. (Year: 2015).*

Beroza et al. Calculation of amino acid pKas in a protein from a continuum electrostatic model: method and sensitivity analysis. Journal of Computational Chemistry, vol. 17, pp. 1229-1244. (Year: 1996).*

Kearnes et al. Molecular graph convolutions: moving beyond fingerprints. Journal of Computer-Aided Molecular Design. vol. 30, Aug. 24, 2016, pp. 595-608.*

European Search Report issued in Application No. 18768749.6, dated Jul. 10, 2019.

Bazeley, Peter S., et al. "Synergistic use of compound properties and docking scores in neural network modeling of CYP2D6 binding: predicting affinity and conformational sampling," J. Chem Inf. Model 206, 46, 2698-2708.

Cang Zixuan, et al. "Representability of algebraic topology for biomolecules in machine learning based scoring and virtual screening,"arXiv: 1708.08135v1, [q-bio.QM], Aug. 27, 2017.

Cheng, Tiejun et al. "Structure-based virtual screening fordrug discovery: a problem-centric review," The AAPS Journal, Vo. 14. No. 1, Mar. 2012, DOI: 10.1202/s12248-012-9322-0.

Melville, James L., et al. "Machine learning in virtual screening," Combinatorial Chemistry & High Throughput Screening, 2009, 12, 332-343.

Song, Chun Meng, et al. "Recent advances in computer-aided drug design," Briefings in Bioinformatics. vol. 10. No 5., 579-591, Advance Access Publication May 11, 2009.

Welch, William, et al. "Hammerhead: fast, fully automated docking of flexible ligands to protein binding sites," Chemistry & Biology, Jun. 1996, 3:449-462.

International Search Report issued in PCT /US2018/033491, dated Aug. 7, 2018.

Pereira et al. "Boosting Docking-Based Virtual Screening with Deep Learning," Journal of Chemical Information and Modeling, Dec. 27, 2016 (Dec. 27, 2016), vol. 56, No. 12, pp. 2495-2506.

* cited by examiner

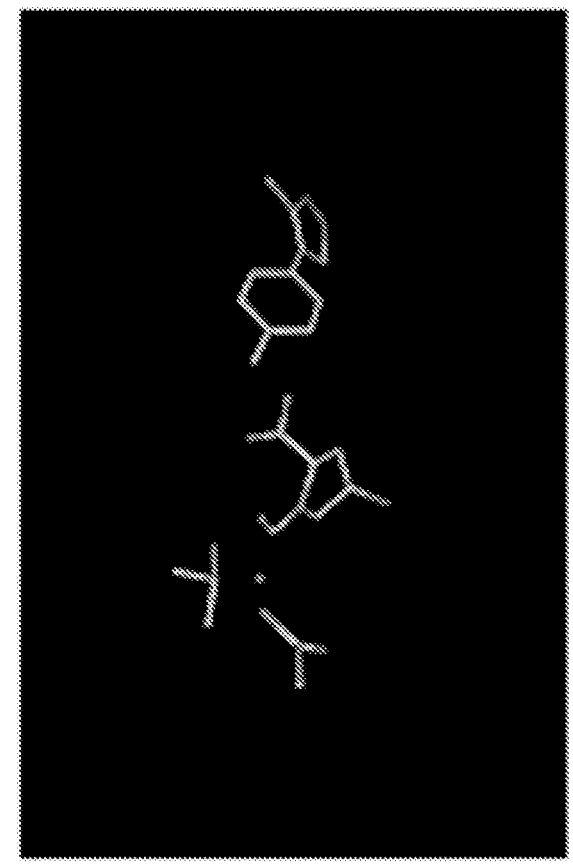
Figure 4b: Bricks of Sample Ligand
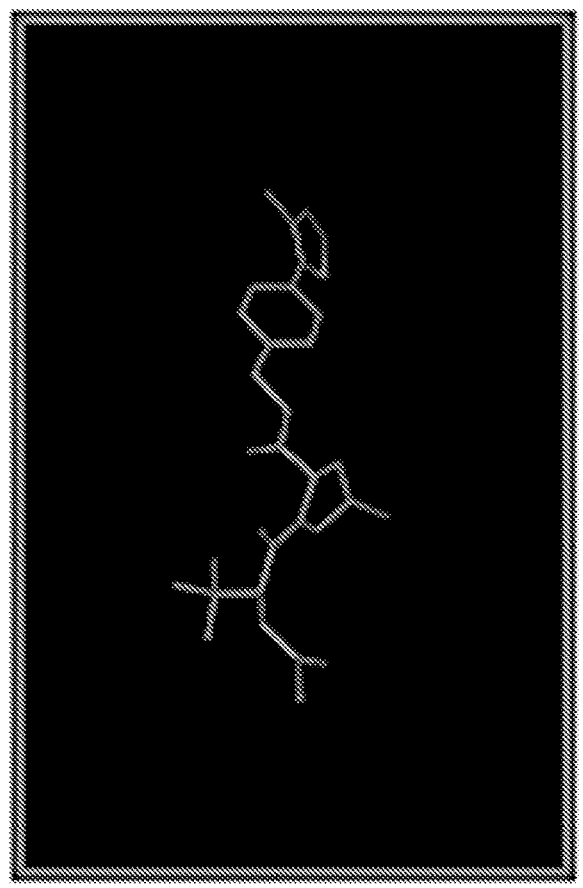
Figure 4a: Sample Ligand

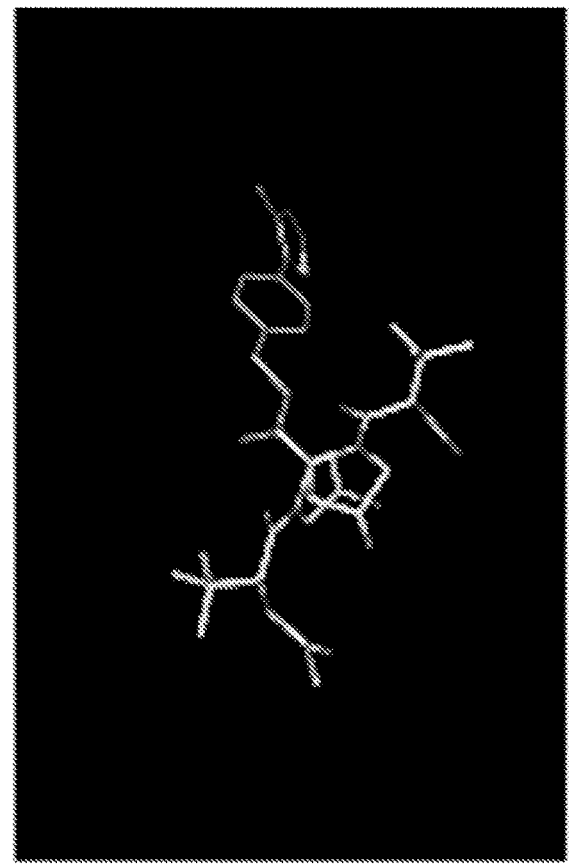
Figure 5b: Double and Triple Bond Dihedral Limited to 0 and 180 Degree Angles
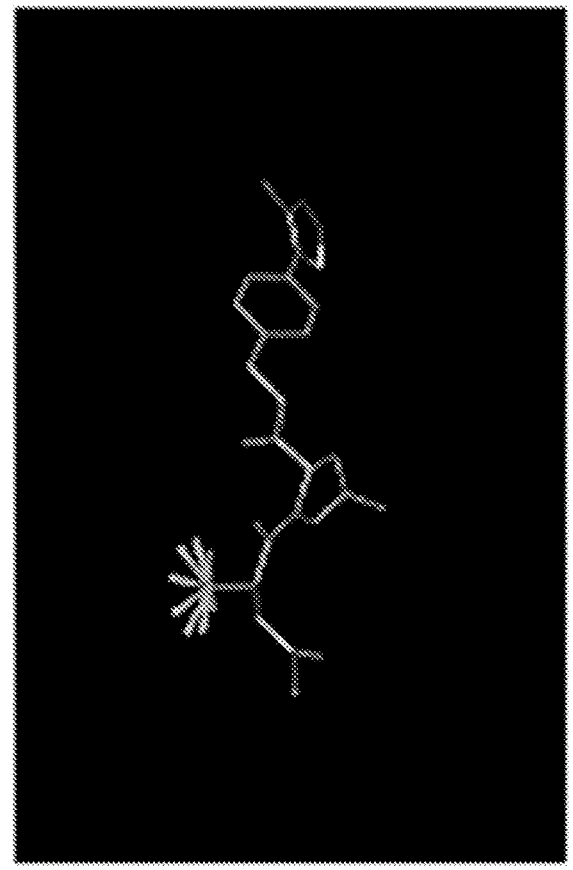
Figure 5a: Single Bond Allowing Full Dihedral Angle Flexibility

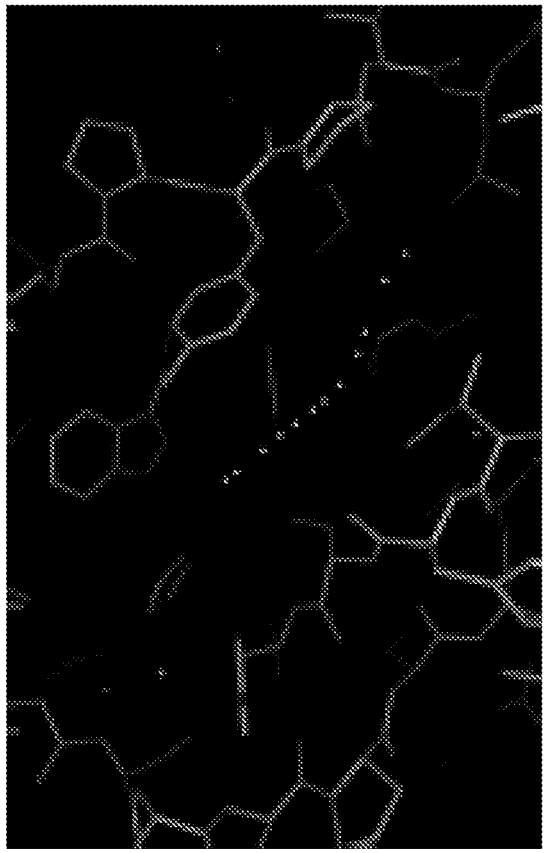
Figure 6b: After Clustering of Pocket Points
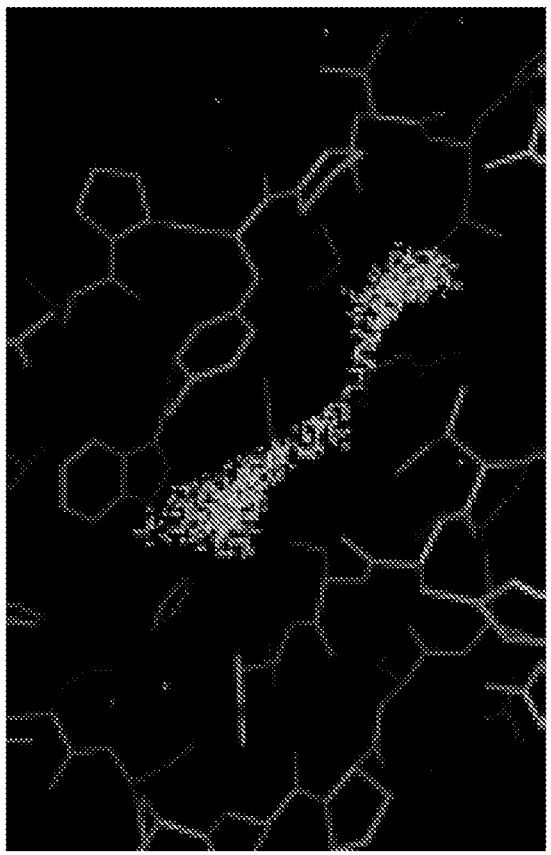
Figure 6a: Pocket Point Identification

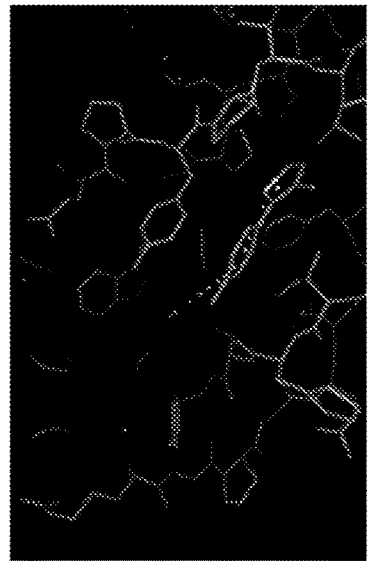
Figure 7a: Anchoring Brick
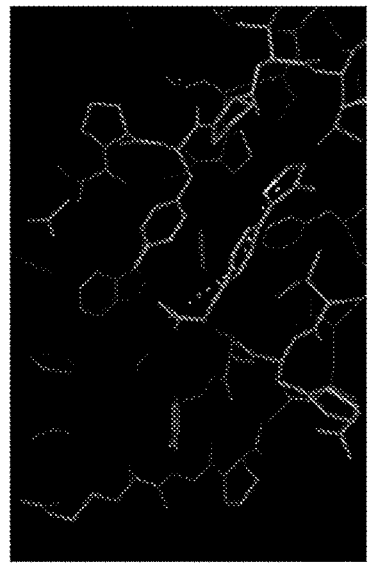
Figure 7b: Growing First Brick
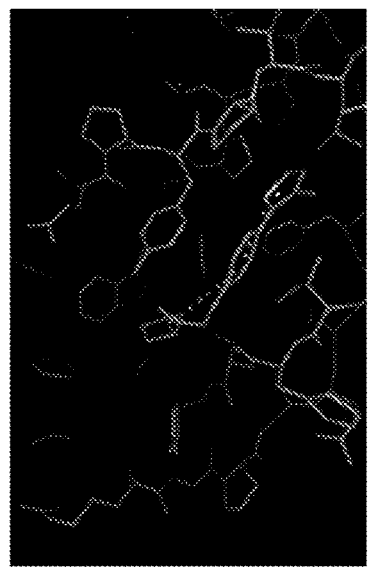
Figure 7c: Growing
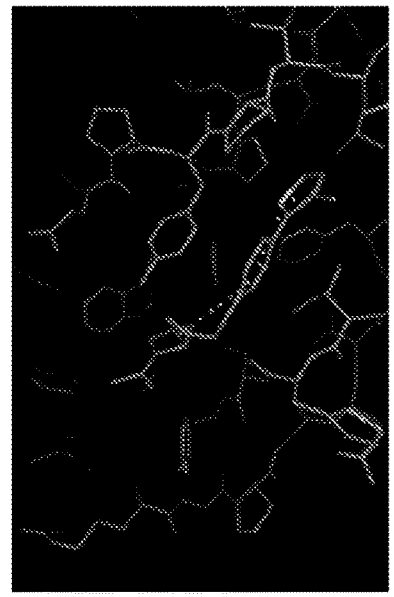
Figure 7d: Growing
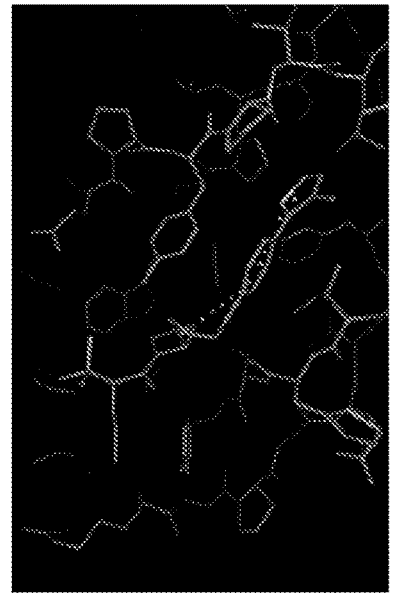
Figure 7e: Growing

Figure 11

Analysis of the mean RMSDs of the top scoring poses of different docking platforms

| | Avg_ShapeRMSD@1 | Avg_ShapeRMSD@5 | Avg_RMSD@1 | Avg_RMSD@5 | SuccessCount |
|---|---|---|---|---|---|
| OrbitalDock | 0.876 | 0.6586 | 1.833 | 1.0852 | 1441 |
| Glide (XP) | 1.5189 | 1.3557 | 2.8675 | 2.5208 | 1438 |
| Glide (SP) | 1.6054 | 1.4736 | 3.0401 | 2.7544 | 1437 |
| Glide (HTVS) | 1.7208 | 1.5806 | 3.6285 | 3.2957 | 1409 |
| UCSF_DEF_FLEXIBLE | 1.5217 | 1.0733 | 3.2183 | 2.139 | 1295 |
| UCSF_DEF_RIGID | 1.8805 | 1.2978 | 4.0144 | 2.6644 | 1321 |
| UCSF_FLX_FLEXIBLE | 1.3526 | 0.8902 | 2.6341 | 1.4847 | 1431 |
| UCSF_FLX_RIGID | 1.831 | 1.2502 | 3.8148 | 2.4975 | 1433 |
| AutoDock Vina | 1.3548 | 0.8959 | 2.77 | 1.5866 | 1433 |
| Rosetta | 1.2917 | 0.9233 | 2.756 | 1.7284 | 1418 |

RMSD = root-mean-square deviation
XP = extra precision
SP = standard precision
HTVS = high-throughput virtual screening

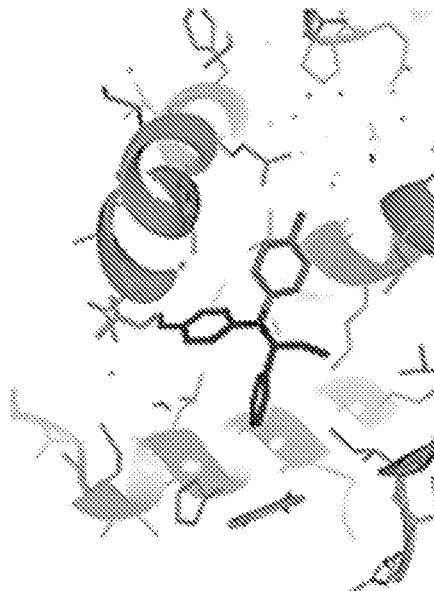
Figure 12b: ER ligand(pdb 3ERT)
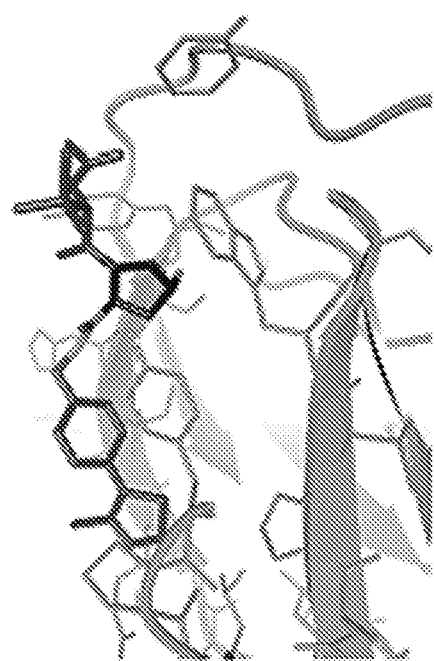
Figure 12a: VHL ligand(pdb 4W9H)
Figure 12c: PPARdelta ligand(pdb 5U3Q)

COMPUTATIONAL METHOD FOR CLASSIFYING AND PREDICTING LIGAND DOCKING CONFORMATIONS

PRIORITY

This application claims priority from U.S. Provisional Patent Application Nos. 62/508,853, filed on May 19, 2017, and 62/560,738, filed on Sep. 20, 2017, the entire contents of all of which are hereby incorporated by reference in the present application.

TECHNICAL FIELD

The present disclosure generally relates to the technical field of computational biology and, more particularly, to computational methods for predicting ligand docking poses, i.e., the preferred conformation and orientation of a small molecule when bound to a protein.

BACKGROUND

Structure-based drug design, also called rational drug design, relies on the knowledge of the three-dimensional structure of the biomolecular target to design ligands that are likely to bind to the target. Structure-based drug design relies on a lock and key hypothesis, where the target is the lock and the ligand is the key. Often, the biomolecular targets are proteins and the ligands are small molecules. Drug docking, and small molecule docking in particular, predicts the preferred conformation and orientation of a small molecule when bound to a protein and has played an increasingly important role in rational drug discovery and design.

Under the lock and key hypothesis, to identify a promising drug target (i.e., a ligand that will bind well to the target), one must understand the lock (i.e., understand the three-dimensional structure of the target and its likely binding regions) and make a good key (i.e., find a ligand that will fit into and bind with one or more of the target's binding regions). The challenges for structure-based drug design in part lie in how to accurately predict the fit of the "lock" and "key" (i.e., the docking structure of the small molecule and protein when they are bound together). For any given peptide sequence, there may be a significant number of biologically relevant conformations, not to mention possible structural reorganization associated with ligand binding. It is thus crucial to accurately predict the changes the protein and the ligand in these drug-target interactions.

The recent increase in deposited structures in the Research Collaboratory for Structural Bioinformatics (RCSB) protein database (PDB), has led to a trend towards structure-based drug design. Small molecule docking plays a central role in this process because under the current "hit-to-lead" stage of the drug discovery process, accurate docking-based virtual screening can potentially identify lead compounds as an alternative to large scale assay-based experimental screens. Second, small molecule docking can potentially avoid the use of otherwise labor-intensive and unpredictable crystallization processes to predict the conformation and orientation of a small molecule when bound to its protein target. This could then serve as a basis for medicinal chemistry optimization. Positive results from recently-reported docking-based drug discovery case studies suggest that this process may form the prelude to a computation-aided drug discovery era (Doman, 2002; Vijayakrishnan, 2009; Talele, 2010; Hartman, 1992).

In the past two decades, over 30 docking-based virtual screening methods/platforms have emerged including: UCSF-Dock (Ewing, 1997), AutoDock Vina (Trott, 2010), Rosetta (Meiler, 2006), and Glide (by Schrödinger) (Friesner, 2006). Most docking procedures typically involve two essential tasks: first, a sampling method is used to search for the potential conformational space of the ligand relative to the binding site; second, a scoring function is used to rank the likelihood of the sampled conformations.

Traditional scoring functions used by currently available docking methods rely heavily on physics-based force field theories combined with certain empirical terms. For example, the following force-fields-based scoring functions are commonly used to model the potential energy of a complex as a summation of bonded and non-bonded interaction energy:

$$E = \sum_{bonds} K_b(b-b_0)^2 + \sum_{angles} K_\theta(\theta-\theta_0)^2 +$$

$$\sum_{torsions} K_\phi[1 + \cos(n\phi - \delta)]$$

$$= \sum_{vdw} \epsilon_{ij}\left[\left(\frac{R_{min,ij}}{r_{ij}}\right)^{12} - 2\left(\frac{R_{min,ij}}{r_{ij}}\right)^6\right] + \sum_{electrostatics} \frac{q_i q_j}{4\pi D r_{ij}}$$

(Huang, 2006).

A drawback of these methods is that some of the empirical terms are not sufficiently accurate. In the equation listed above, for example, in the van der Waals (vdW) energy terms represented by Lennard-Jones 12-6 function, the use of $r^{12}$ in repulsive term and $r^6$ in attractive term are not accurate in some cases. Furthermore, current physics-based scoring functions are essentially an approximation of a static energy function (Huang, 2006), which fails to capture the otherwise thermodynamic nature of the ligand-receptor binding process. Thus, the reliance on these equations leads to inaccurate scoring and ranking of small molecule docking.

To address some of these issues, molecular dynamics approaches may be used. For example, the free energy perturbation (FEP) method (Zwanzig, 1954) may approximate the free energy difference of ligand binding using direct thermodynamics sampling and simulations. Recently, the FEP method has been adopted for ligand potency prediction using the Schrödinger platform (Wang, 2015). But these methods still rely on physics-based computations to score potential complexes.

Additionally, traditional docking methods/platforms only consider a single binding site at a time. That is, traditional scoring functions do not consider that a ligand may be able to bind to a protein at multiple sites. As a hypothetical, ligand A may have a low affinity to binding site A but a high affinity to binding site B. In traditional methods—because only one binding site may be considered at a time—if only binding site A is considered, then ligand A may be overlooked as a potential new drug despite its high affinity to binding site B.

Furthermore, traditional methods are more laborious. In practice, molecular dynamics simulations are computationally very expensive and are often not feasible for large scale virtual screening tasks.

Additionally, current methods do not necessarily identify the specific portions of a ligand critical to docking. The ligand portions important for the binding reaction are indicative of the pharmacophore of the ligand.

Accordingly, there is a need to develop a reliable and efficient method to accurately predict small molecule docking conformation. The disclosed methods and systems are directed to overcoming one or more of the problems and/or difficulties set forth above, and/or other problems of the prior art.

SUMMARY

According to a first aspect of the present disclosure, a method for predicting the docking pose of a compound is provided. The method may include obtaining structure data representing a plurality of conformations of a compound. The method may also include determining structural differences among the conformations. The method may also include construction of a dynamic deep neural network to quantize, rank the relative likelihood of sampled ligand conformation. The method may also include determining the pharmacophore of a bound ligand based on the omitting score calculated by the deep neural network.

According to one aspect of the disclosure, a computer-implemented method for predicting a conformation of a ligand docked into a protein is disclosed comprising determining one or more poses of the ligand, the poses being representative conformations of the ligand; extracting features associated with the poses of the ligand; constructing, based on the extracted features, feature vectors associated with the poses of the ligand; determining, using a neural network, scores associated with the poses; and determining a proper conformation for the docked ligand based on the scores.

In certain embodiments, determining one or more poses of the ligand comprises dividing the ligand into two or more sections; anchoring a first section of the two or more ligand sections to a location of the protein; adding at least one subsequent section of the two or more ligand sections to the first section to form a growing ligand; and continuing adding subsequent sections to the growing ligand until the ligand is complete.

In certain embodiments, the extracted features comprise features of a first atom and features of the interaction between the first atom and a second atom. In certain embodiments the features of the first atom comprise one or more of an atom type, a radius of the atom, a number of rings in which the atom is included, a size of the ring in which the atom is included, whether the first atom is part of an aromatic ring, and the pairwise potential of the first atom. In certain embodiments, the pairwise potential of the first atom comprises the sum of the pairwise atom potentials between the first atom and atoms of the protein. In certain embodiments, the features of the interaction between the first atom and the second atom comprise one or more of a bond type, a distance between the first and second atoms, and whether the first and second atoms are in the same ring.

In certain embodiments, the constructed feature vectors comprise a dense feature vector for each atom of the ligand, wherein each dense feature vector including the features of an atom and features of the interaction between that atom and another atom.

In certain embodiments, determining, using a neural network, scores associated the poses comprises at least one convolution of the feature vectors associated with the poses of the ligand. In certain embodiments, determining, using a neural network, scores associated the poses comprises two convolutions of the feature vectors associated with the poses of the ligand.

In certain embodiments, the convolution of each feature vector comprises a transformation operator and a reduction operator. In certain embodiments, the transformation operator comprises transforming the feature vectors of neighbor atoms of an atom of interest by a feed-forward linear sub-network. In certain embodiments, the feature vector of each neighbor atom comprises a dense feature vector, the dense feature vector comprises an atom feature vector for the neighbor atom and an atom pair feature vector for the neighbor atom and the atom of interest, and the dense feature vector is input into the transformation operator as a concatenation of the atom feature vector and the atom pair feature vector, and the input is transformed through a fully connected layer and a non-linearity function. In certain embodiments, the reduction operator comprises aggregating the transformed feature vectors of neighbor atoms of the atom of interest; applying a commutative reduction function to the aggregated transformed feature vectors of neighbor atoms of an atom of interest to produce a reduced feature map for the atom of interest. In certain embodiments, the convolution process further comprises an optimization operator that combines the initial feature vector of an atom of interest with the feature vector output after the application of the transformation operator and reduction operator, resulting in a final feature vector for the atom of interest.

In certain embodiments, determining, using a neural network, scores associated the poses comprises applying a scoring function to the feature vectors of the atoms of the ligand for each pose. In certain embodiments, the scoring function is a weighted scoring function that applies a weighted vector to the feature vectors of the atoms of the ligand for each pose, wherein the weighted vector is determined by a machine-learning algorithm. In certain embodiments, the machine-learning algorithm for determining the weight vector is trained on real-world protein structure data. In certain embodiments, the training of the machine-learning algorithm comprises determining a weight vector $\vec{W}=(w_1, w_2, w_3, \ldots, w_n)$ for the real-world protein structure data, where, when the feature vector for the correct ligand conformation equals $(x_1, x_2, x_3, \ldots, x_n)$ and the feature vector for an incorrect ligand conformation is $(y_1, y_2, y_3, \ldots, y_n)$, $\vec{W}$ satisfies the equation $(\Sigma_{i=1}^{n} w_i x_i - \Sigma_{i=1}^{n} w_i y_i) > 0$; wherein $w_i$ is the weight vector for instance i.

In certain embodiments, determining a proper conformation for the docked ligand based on the scores comprises ranking the scores associated with the ligand poses.

According to one embodiment, a computer-implemented method for predicting a conformation of a ligand docked into a protein is disclosed, the method comprising dividing the ligand into two or more sections; anchoring a first section of the two or more ligand sections to a location of the protein; determining, using a neural network, a score associated with the anchored first section; and determining a proper conformation for the docked ligand based on the scores.

In certain embodiments, determining one or more poses of the ligand comprises dividing the ligand into two or more sections; anchoring a first section of the two or more ligand sections to a first location of the protein; anchoring a second section of the two or more ligand sections to a second location of the protein, wherein the second location of the protein may be the same or different than the first location of the protein; extracting features associated with the anchored first section of the ligand and features associated with the anchored second section of the ligand; constructing, based on the extracted features, feature vectors associated with the anchored first section of the ligand and feature vectors associated with the anchored second section of the ligand; determining, using a neural network, scores associated with the anchored first section and anchored second section; and determining a proper anchor for the docked ligand based on the scores.

According to one embodiment, a computer-implemented method for predicting an anchor section of a ligand docked into a protein is disclosed, the method comprising dividing the ligand into two or more sections; anchoring a first section of the two or more ligand sections to a first location of the protein; anchoring a second section of the two or more ligand sections to a second location of the protein, wherein the second location of the protein may be the same or different than the first location of the protein; extracting features associated with the anchored first section of the ligand and features associated with the anchored second section of the ligand; constructing, based on the extracted features, feature vectors associated with the anchored first section of the ligand and feature vectors associated with the anchored second section of the ligand; determining, using a neural network, scores associated with the anchored first section and anchored second section; and determining a proper anchor for the docked ligand based on the scores.

According to one embodiment, a computer-implemented method for predicting a conformation of a potential growing ligand section docked into a protein is disclosed, the method comprising dividing the ligand into a plurality of sections; creating a first growing ligand section by anchoring a first section of the plurality of sections to a first location of the protein and adding a second section of the plurality of sections to the first section in a first conformation; creating a second growing ligand section by anchoring a first section of the plurality of sections to a first location of the protein and adding a second section of the plurality of sections to the first section in a second conformation; extracting features associated with the first growing ligand section and features associated with the second growing ligand section; constructing, based on the extracted features, feature vectors associated with the first growing ligand section and feature vectors associated with the second growing ligand section; determining, using a neural network, scores associated with the first growing ligand section and the second growing ligand section; and determining a potential growing ligand section for the docked ligand based on the scores.

According to one embodiment, a computer-implemented method is disclosed for predicting a pharmacophore of a ligand docked into a protein, the method comprising removing a section of the ligand; determining one or more poses of the largest remaining portion of the ligand, the poses being representative conformations of the ligand; extracting features associated with the poses of the ligand; constructing, based on the extracted features, feature vectors associated with the poses of the remaining portion ligand; determining, using a neural network, rerank scores of the poses; and assigning the best rerank score of the poses to removed section of the ligand.

In certain embodiments, a lower rerank score is associated with a higher probability that the removed section is a pharmacophore.

In certain embodiments, the method further comprises repeating the steps with a second section of the ligand to assign a best rerank score of the poses to the second removed section; and ranking the first rerank score and the second rerank score to determine the likelihood that the first removed section is a pharmacophore as compared to the second removed section.

In certain embodiments, the methods disclosed further comprise generating a graphical representation of the predicted conformation of the ligand.

In certain embodiments, the methods further comprise generating a graphical representation of the anchor section of the ligand.

In certain embodiments, the methods disclosed further comprise generating a graphical representation of the potential growing ligand section.

In certain embodiments, the methods disclosed further comprise generating a graphical representation of the pharmacophore of the ligand.

According to certain embodiments, a non-transitory computer readable medium is disclosed for performing the methods disclosed.

According to certain embodiments, a system is disclosed for performing the methods disclosed. In certain embodiments, the system is a distributed system.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate embodiments consistent with the present disclosure and, together with the description, serve to explain the principles of the present disclosure.

FIG. 4a is a schematic diagram of an exemplary ligand.

FIG. 4b is a schematic diagram of the exemplary ligand of FIG. 4a split into bricks according to certain exemplary embodiments.

FIG. 5a illustrates an example of the pose library for a single bond, i.e., the variations conformational poses based on rotation around the single bond of the exemplary ligand of FIG. 4A, according to certain exemplary embodiments.

FIG. 5b illustrates an example of the pose library for double and triple bonds, i.e., the 0 degree and 180 degree angles of the pentagonal ring of the exemplary ligand of FIG. 4a, according to certain exemplary embodiments.

FIG. 6a shows the pocket points identified for a particular target, according to certain exemplary embodiments.

FIG. 6b shows the results of clustering the identified pocket points of the target, according to certain exemplary embodiments.

FIGS. 7a-7e illustrate the anchor and grow method of identifying ligand conformations for given target pocket points, according to certain exemplary embodiments.

FIG. 11 provides exemplary results of an exemplary embodiment of the disclosed neural network model (OrbitalDock) compared to known docking platforms.

FIG. 12a provides an example of an omitting score heat map for the von Hippel-Lindau (VHL) ligase ligand (with the Hypoxia Inducible Factor (HIF) Alpha Subunit as target) (PDB 4W9H) according to certain exemplary embodiments.

FIG. 12b provides an example of an omitting score heat map for the Human Estrogen Receptor Alpha (ERα) ligand (with 4-Hydroxytamoxifen as target) (PDB 3ERT) according to certain exemplary embodiments.

FIG. 12c provides an example of an omitting score heat map for the Human PPARdelta ligand (with specific agonist 1 as target) (PDB 5U3Q) according to certain embodiments.

DETAILED DESCRIPTION

Figure 1:
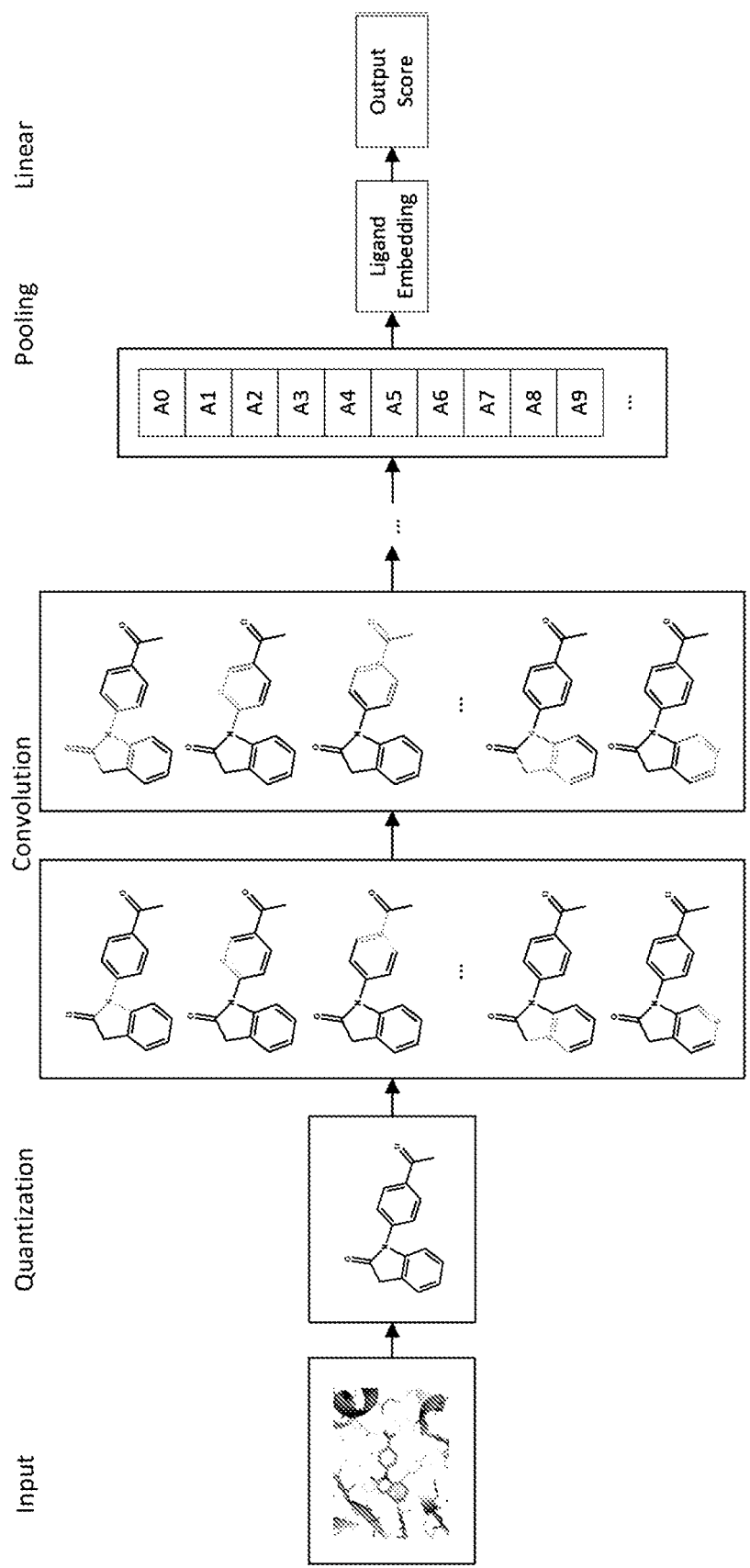
FIG. 1 is a flowchart of an example of a neural network architecture according to one embodiment.

Reference will now be made in detail to exemplary embodiments, examples of which are illustrated in the accompanying drawings. The following description refers to the accompanying drawings in which the same numbers in different drawings represent the same or similar elements unless otherwise represented. The implementations set forth in the following description of exemplary embodiments do not represent all implementations consistent with the present disclosure. Instead, they are merely examples of devices and methods consistent with aspects related to the invention as recited in the appended claims.

The docking task is often needed in the following three stages of the drug discovery process: (1) to predict the binding conformation of a known active ligand; (2) to enable a virtual screening to identify new ligands, which is aimed at discovering new leading drugs; and (3) to predict the binding affinities of untested compounds to a target site (Leach 2006). The goal of docking prediction, including small molecule docking prediction, is to identify the most likely conformations of a ligand to a target and to rank the ligand docking poses.

Docking involves two essential tasks: a ligand sampling method to identify potential ligand poses (i.e., conformational structures) and an evaluation system to rank the likelihood of the sampled ligand poses.

The present disclosure provides a computational approach to predict ligand docking, such as small molecule docking to a target protein. Instead of relying on a physics or empirical terms based force field-derived scoring function, the present disclosure provides a purely data-driven dynamic neural network architecture that was designed and trained to rank the sampled ligand docking poses.

An exemplary embodiment of the disclosed systems and methods was designed, called "OrbitalDock." As disclosed herein, to train the system, a large scale redocking study was developed using over 1,000 co-crystal structures in which the system had no information regarding the correct docking poses of the starting ligands. After training, the exemplary OrbitalDock system was nearly twice as accurate as current standard methods, including Glide (Schrödinger), UCSF-dock, Rosetta, and AutoDock Vina. Importantly, this improved performance was accomplished without use of information regarding the chemistry or physics of the ligands and their targets. Furthermore, the OrbitalDock system embodying the disclosed systems and methods could identify specific portions of the ligand critical to the binding reaction based on an omitting and re-ranking method, which was indicative of the pharmacophore of the ligands.

Instead of relying on physics-based or molecular dynamics approaches, a computationally more efficient alternative is the fingerprint-based method. In this approach, certain substructures or important interactions in a ligand useful for molecular recognition and binding are identified. These "fingerprints" or "pharmacophores" typically include aromatic rings, hydrophobic centroids, hydrogen bond donors and acceptors. A fingerprint-based method learns important features from known high affinity receptor-ligand complexes which are then used to predict ligand binding likelihood for other ligands.

A deep neural network capable of learning some important chemical features is disclosed in U.S. application Ser. No. 15/591,075, filed May 9, 2017, published as U.S. Patent Publication No. 2017-0329892, hereby incorporated by reference. The deep neural network was able to predict the amino acid side chain conformation, outperforming the standard method, SCWRL4, by over 25% across amino acid types.

The present disclosure advances that work, extending the use of the statistical learning method and developing an exemplary OrbitalDock system, a 4-layer deep neural network architecture, to rank the sampled ligand poses without providing the system prior chemistry and physics domain knowledge.

As described herein, a large-scale redocking study using 1,441 available high quality co-crystal structures was carried out to compare the relative accuracy of OrbitalDock with current standard methods. In this study, OrbitalDock was found to be superior to current standard methods; it was nearly twice as accurate as current standard methods including Schrödinger, UCSF-dock, and Rosetta.

Overview of Deep Neural Network Based Model

Traditional fingerprint and pharmacophore methods usually require that explicit features are extracted and trained, hence the forms of the fingerprints are often limited by human prior knowledge. To address this issue and others, a deep neural network architecture is disclosed that provides a ligand docking pose ranking system.

The overall neural network architecture is shown in FIG. 1. As shown in FIG. 1, the deep neural network accepts a sampled receptor-ligand complex is quantized using inputs include a static pairwise potential score system, and it outputs the probability or feasibility score of a given ligand pose or conformational structure.

As shown in FIG. 1, after the input atom and atom pair features are quantized for each atom in the ligand, the feature vectors are fed through a series of graph-based convolution operators. The convolution process is described in more detail below. Each convolution operation transforms the dense feature vectors and assigns weights to them (described below). The set of dense feature vectors that result from the convolution process are reduced to a single dense feature vector, called a feature map, which is further transformed through several fully connected layers to obtain a final feasibility score for the ligand's conformation.

The final feasibility score can then be used to rank the various ligand conformations and/or otherwise predict the binding of the ligand/protein complex.

Input Quantization

To be used by the computer-based system, the input must be quantized. The input of the system may be, for example, structural information regarding a small molecule, a ligand, a ligand-receptor complex, etc. The protein structural information used in the disclosed embodiments may be extracted from the PDB data, which may be organized in various file formats, such as PDB file format, Extensible Markup Language (XML) file format, or macromolecular Crystallographic Information File (mmCIF) format. For illustrative purpose only, this disclosure assumes the PDB data is represented as PDB files. However, it is contemplated that the PDB data used by the disclosed methods may be represented in any format.

The quantization of the input may be conducted in a variety of ways. The system may derive quantized information on the input based on its chemical formula, a chemical name, a high-resolution image of the crystal structure, a chemical drawing, data about the molecule, data about the atoms comprising the molecule, data about atom interactions, or any other method known to one of ordinary skill in the art for providing information to the system regarding the structure of the molecule (e.g., the type of atom and the other atoms to which each atom is bonded).

In an exemplary embodiment, the inputs are quantized as dense feature vectors for each atom and atom pair. The dense feature vectors may take the form of $A_a$, $P_{(a,b)}$, with $A_a$ defined as the feature vector of atom a, and $P_{(a,b)}$ defined as the feature vector of atom pair a and b.

Table 1 provides a list of exemplary atom features that may comprise a feature vector for atom a. Typical atom features include atom type, atom radius, and whether the atom is in an aromatic ring.

TABLE 1

| Atom feature | Description | Size |
| --- | --- | --- |
| Atom type | One hot vector specifying the type of this atom. | 23 |
| Radius | van der Waals radius and covalent radius of the atom. | 2 |
| In rings | For each size of ring (3-8), the number of rings that include this atom. | 6 |
| In aromatic ring | Whether this atom is part of an aromatic ring | 1 |
| Pairwise potential | Sum of pairwise atom potential between this atom and receptor atoms. | 1 |

As shown in Table 1, in exemplary embodiments, the type of atom may be provided to the system by entering one value (i.e., one hot vector), wherein each value corresponds to an atom type, such as the 23 atom-types detailed Table 1a. Atom types are essential for ranking the potential energies of the possible side chain conformations. The disclosed embodiments presume that atoms with the same electronic, chemical, and structural properties share the same atom type, and classify each atom by its neighboring atoms and bonds.

Several strategies have been developed in the related art to define the atom types, such as the strategies described in, e.g., Summa C M, Levitt M, DeGrado W F, An atomic environment potential for use in protein structure prediction, *Journal of Molecular Biology* (2005) 352(4): 986-1001; or the CHARMM force field (see www.charmm.org). These strategies are incorporated in the present disclosure by reference.

Figure 14:
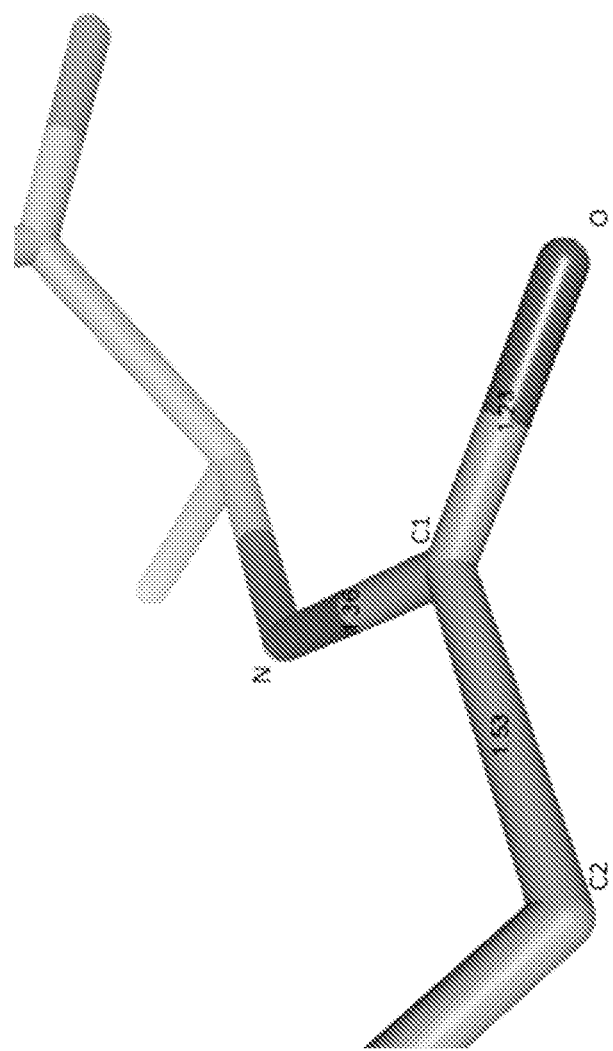
FIG. 14 provides a schematic diagram illustrating an example of a local structure of a protein side chain, according to an exemplary embodiment.

In addition, the present disclosure provides the following method for generating the atom types:

1. Extract information regarding the bond environment of each atom in the amino acids of a protein. The bond environment may include: the element of the atom at question, the bond lengths of the atom at question, and the elements of the atoms bonding with the atom at question. For example, FIG. 14 is a schematic diagram illustrating a local structure of an amino acid side chain. Referring to FIG. 14, the bond environment for atom C1 may be presented as: (C, (1.23, 1.36, 1.53)). That is, the element of the atom at question is carbon. The atom's bond lengths are 1.23 Å, 1.36 Å, and 1.53 Å, respectively.

2. Classify the atoms into one or more clusters according to the atoms' bond environments. The atoms in the same cluster have similar bond environments. Any of the above-described clustering methods, e.g., K-means clustering method or spectral clustering method, may be used to classify the atoms.

3. Assign a unique atom type to each cluster.

In one embodiment, atoms found in the 20 common amino acids are classified into 23 atom types, using the above-describe method. Any unclassified atoms are classified as "unknown atom type."

As indicated in Table 1a, certain embodiments may only require information on non-hydrogen atoms (e.g., various types of carbon, oxygen, nitrogen, and sulfur), and individual hydrogen may not be considered and/or information about hydrogen atoms may not be entered into the system. In certain embodiments, information about the hydrogen atoms in the molecule may be derived from and/or assumed by the system based on the types of non-hydrogen atoms present in the molecule.

TABLE 1a

| Type | Atoms |
| --- | --- |
| 1 | ALA C; ARG C; ASN C; ASN CG; ASP C; CYS C; GLN C; GLN CD; GLU C; GLY C; HIS C; ILE C; LEU C; LYS C; MET C; PHE C; PRO C; SER C; THR C; TRP C; TYR C; VAL C; |
| 2 | ALA $C^\alpha$; ARG $C^\alpha$; ASN $C^\alpha$; ASP $C^\alpha$; CYS $C^\alpha$; GLN $C^\alpha$; GLU $C^\alpha$; HIS $C^\alpha$; ILE $C^\alpha$; LEU $C^\alpha$; LYS $C^\alpha$; MET $C^\alpha$; PHE $C^\alpha$; PRO $C^\alpha$; SER $C^\alpha$; THR $C^\alpha$; THR $C^\alpha$; TRP $C^\alpha$; TYR $C^\alpha$; VAL $C^\alpha$; |
| 3 | ALA $C^\beta$; ILE $C^{\delta}_1$; ILE $C^{\gamma}_2$; LEU $C^{\delta}_1$; LEU $C^{\delta}_2$; THR $C^{\gamma}_2$; VAL $C^{\gamma}_1$; VAL $C^{\gamma}_2$; |
| 4 | ALA N; ARG N; ARG $N^\epsilon$; ASN N; ASP N; CYS N; GLN N; GLU N; GLY N; HIS N; ILE N; LEU N; LYS N; MET N; PHE N; SER N; THR N; TRP N; TYR N; VAL N; |
| 5 | ALA O; ARG O; ASN O; ASN $O^{\delta}_1$; ASP O; ASP $O^{\delta}_1$; ASP $O^{\delta}_2$; CYS O; GLN O; GLN $O^{\epsilon}_1$; GLU O; GLU $O^{\epsilon}_1$; GLU $O^{\epsilon}_2$; GLY O; HIS O; ILE O; LEU O; LYS O; MET O; PHE O; PRO O; SER O; THR O; TRP O; TYR O; VAL O; |
| 6 | ARG $C^\beta$; ARG $C^\gamma$; ASN $C^\beta$; ASP $C^\beta$; GLN $C^\beta$; GLN $C^\gamma$; GLU $C^\beta$; GLU $C^\gamma$; HIS $C^\beta$; ILE $C^{\gamma}_1$; LEU $C^\beta$; LYS $C^\beta$; LYS $C^\delta$; LYS $C^\epsilon$; LYS $C^\gamma$; MET $C^\beta$; PHE $C^\beta$; PRO $C^\beta$; PRO $C^\delta$; PRO $C^\gamma$; TRP $C^\beta$; TYR $C^\beta$; |
| 7 | ARG $C^\delta$; GLY $C^\alpha$; SER $C^\beta$; |
| 8 | ARG $C^\zeta$; |
| 9 | ARG $N^{\eta}_1$; ARG $N^{\eta}_2$; ASN $N^{\delta}_2$; GLN $N^{\epsilon}_2$; |
| 10 | ASP $C^\gamma$; GLU $C^\delta$; |
| 11 | CYS $C^\beta$; MET $C^\gamma$; |
| 12 | CYS $S^\gamma$; |

TABLE 1a-continued

| Type | Atoms |
|---|---|
| 13 | HIS $C^\delta_2$; HIS $C^\epsilon_1$; PHE $C^\delta_1$; PHE $C^\delta_2$; PHE $C^\epsilon_1$; PHE $C^\epsilon_2$; PHE $C^\zeta$; TRP $C^\delta_1$; TRP $C^\epsilon_3$; TRP $C^\eta_2$; TRP $C^\zeta_2$; TRP $C^\zeta_3$; TYR $C^\delta_1$; TYR $C^\delta_2$; TYR $C^\epsilon_1$; TYR $C^\epsilon_2$; |
| 14 | HIS $C^\gamma$; PHE $C^\gamma$; TYR $C^\gamma$; |
| 15 | HIS $N^\delta_1$; HIS $N^\epsilon_2$; TRP $N^\epsilon_1$; |
| 16 | ILE $C^\beta$; LEU $C^\gamma$; VAL $C^\beta$; |
| 17 | LYS $N^\zeta$; |
| 18 | MET $C^\epsilon$; |
| 19 | MET $S^\delta$; |
| 20 | PRO N; |
| 21 | SER $O^\gamma$; THR $O^\gamma_1$; TYR $O^\eta$; |
| 22 | TRP $C^\delta_2$; TRP $O^\epsilon_2$; TYR $C^\zeta$; |
| 23 | TRP $C^\gamma$; |

As shown in exemplary Table 1, in certain embodiments, two values may be entered for the atom radius: (1) the van der Waals radius, and (2) the covalent radius of the atom.

As shown in exemplary Table 1, in certain embodiments, information on both the size and number of rings to which the atom belongs is entered. For example, a single atom may be part of 1 ring of 5 atoms and 1 ring of 6 atoms.

As shown in exemplary Table 1, in certain embodiments, information on whether the atom is part of an aromatic ring may be entered.

As shown in exemplary Table 1, in certain embodiments, a value representing the sum of the pairwise atom potential between the atom and protein receptor atoms may be entered. Details regarding the calculation of pairwise potentials may be found in U.S. application Ser. No. 15/591,075, filed May 9, 2017, which is hereby incorporated by reference in its entirety.

In brief, a scoring function H(x) may be applied to a ligand atom and a receptor atom to obtain a score representing the interaction for that pair of atoms. All interactions between the ligand atom and potentially many receptor atoms are scored using the H(x) function. The sum of these scores is the pairwise potential of that ligand atom. The H(x) function may be developed by machine learning algorithms, such as the H(distance, anglescore) function described below.

The pairwise potential score may be used in multiple steps in the process. For example, the ligand's pairwise potential score may be used as a weak scoring function in the anchor and grow process for the initial sampling of ligand poses. In the neural network model, the pairwise potential score of an atom may be used as one feature for each atom, as shown in the last row of Table 1, above.

An atom's pairwise potential relates to forces between that atom and atoms of the receptor protein, such as van der Waals force and electrostatic force. The force between two atoms is determined by the type of the atoms, the distances between the atoms, and the angle between the force and the bonds of the atoms. For example, traditional force field methods, including CHARMM, use several type of pairwise potentials, such as Lennard-Jones and electrostatic terms. (See, e.g., MacKerell, 1998.)

In some embodiments, different terms of the atom pairwise potential may be merged. For example, if the atom pairwise potential includes a term $F_1$ expressed in $F_1$(distance), a term $F_2$ expressed in $F_2$ (distance), then a new term F may be defined according to: F(distance $F_1$(distance)+$F_2$ (distance). Therefore, any number of explicit pairwise energy functions can be merged to a single implicit scoring function H(x), which may be the H(distance, anglescore) function introduced below. This way, the pairwise potential is described by implicit potential terms instead of explicit potential terms.

Figure 16:
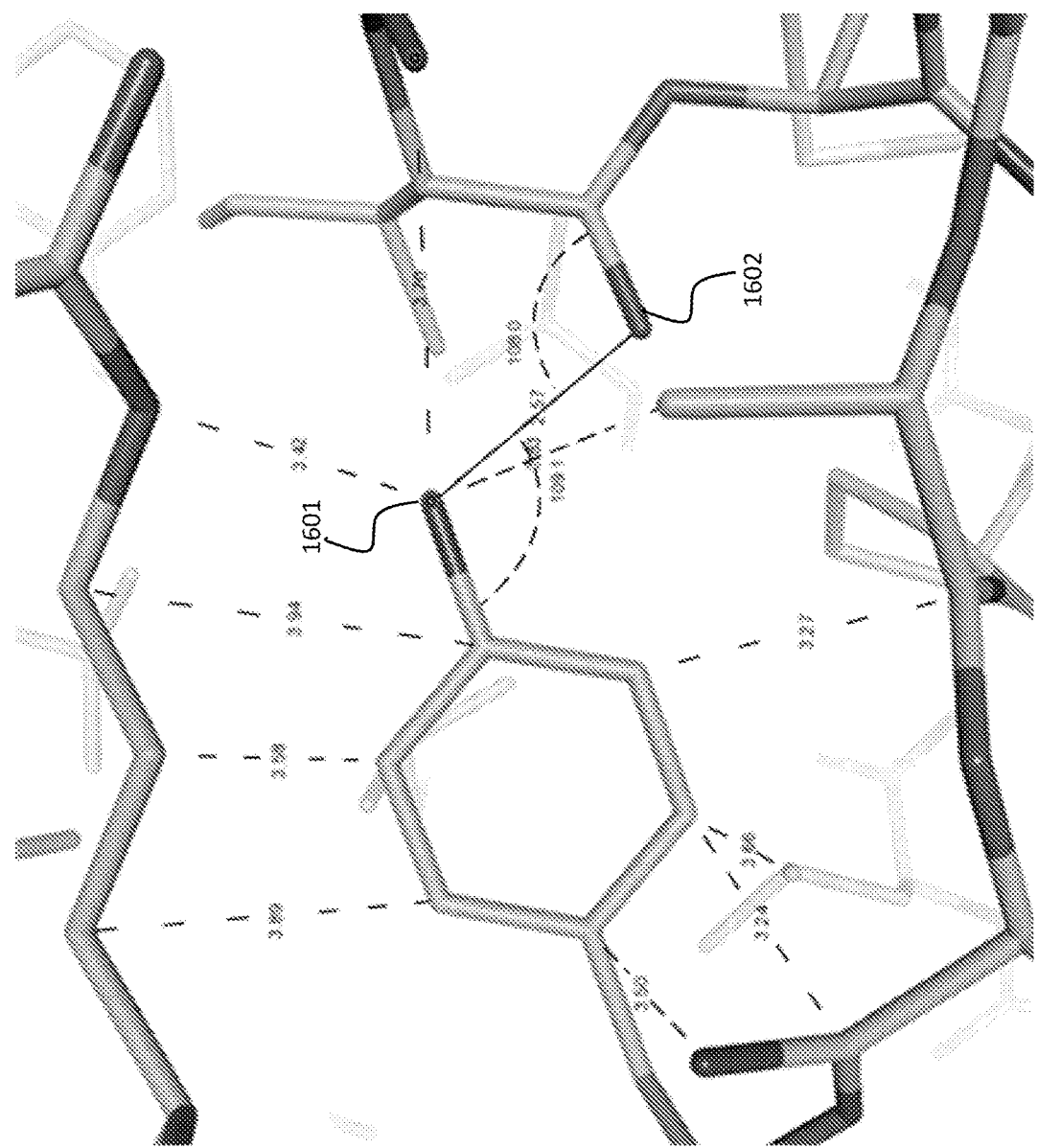
FIG. 16 is a schematic diagram illustrating an example of pairwise interaction between two atoms.

Besides distances between the atoms, the pairwise potential also depends on the direction of the pairwise interactions between the atoms. The direction is particularly important in the cases involving polar atoms. Generally, bonded atoms contributed more to the pairwise potential than non-bonded atoms. FIG. 16 is a schematic diagram illustrating pairwise interaction between two atoms. Referring to FIG. 16, the distance between two oxygen atoms (identified as 1601 and 1602) is 2.57 Å, and the angles between the pairwise force vector and the bonds associated with the two oxygen atoms are 109.1° and 108.0°, respectively. An angle score may be defined to measure the influence of the bonds on the pairwise potential. The angle score is the dot product between an atom's pairwise force vector and bond vector. For an atom with more than one covalent bond, the dot product is between the atom's pairwise force vector and the sum of all the bond vectors. The angle score may be normalized and thus have a range of [−1,1].

Figure 17B:
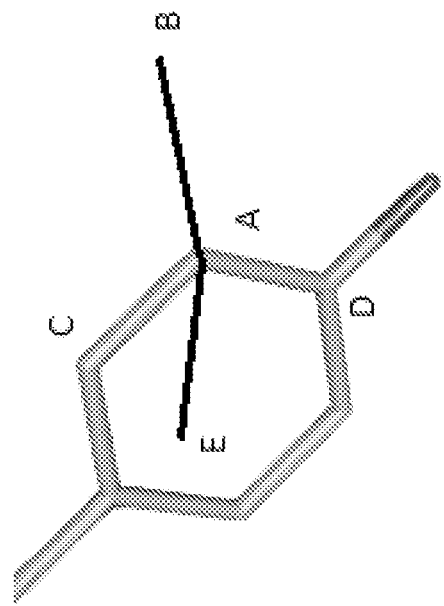
FIG. 17b is a schematic diagram illustrating an example of multiple pairwise interactions associated with an atom that has two covalent bonds, according to an exemplary embodiment.
Figure 17A:
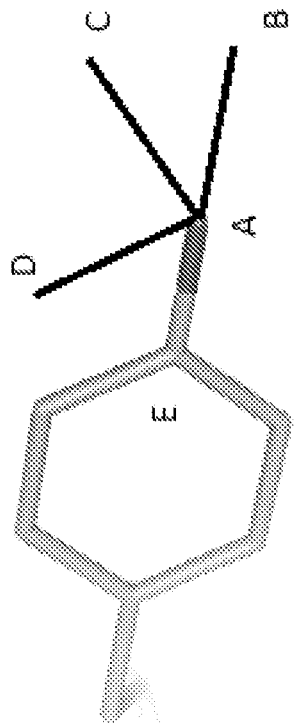
FIG. 17a is a schematic diagram illustrating an example of multiple pairwise interactions associated with an atom that has a covalent bond, according to an exemplary embodiment.

FIG. 17a is a schematic diagram illustrating multiple pairwise interactions associated with an atom that has a covalent bond. Referring to FIG. 17a, the oxygen atom A has only one covalent bond. The covalent bond is represented by the vector EA. An angle score of atom A may be defined as the dot product between a pairwise force vector associated with atom A and the bond vector $\overrightarrow{EA}$. For example, the pairwise interaction formed between atom A and atom B has the highest possible angle score, since $\overrightarrow{EA} \cdot \overrightarrow{AB} = 1$. Conversely, the pairwise interaction formed between atom A and atom E has the lowest angle score since $\overrightarrow{EA} \cdot \overrightarrow{AE} = -1$. Moreover, the pairwise interactions formed between atom A and atom C or D have an angle score in between −1 and 1.

FIG. 17b is a schematic diagram illustrating multiple pairwise interactions associated with an atom that has two covalent bonds. Referring to FIG. 17b, atom A has two bond vectors $\overrightarrow{CA}$ and $\overrightarrow{DA}$. The pairwise interaction formed between atom A and atom B has a pairwise force vector $\overrightarrow{AB}$, which is in the same direction as the net vector $\overrightarrow{CA} + \overrightarrow{DA}$. Accordingly, the pairwise interaction formed between atom A and atom B has the highest angle score. Conversely, pairwise force vector $\overrightarrow{AE}$ is in the opposite direction of the net vector $\overrightarrow{CA} + \overrightarrow{DA}$, and thus the pairwise interaction formed between atom A and atom E has the lowest angle score. For atoms with more than two covalent bonds, the angle score is similarly defined.

After the distances and angle scores are determined, the atom pairwise potential energy may be determined. For each pair of atoms in a certain molecular environment, there may be a unique function H(distance,anglescore) based on atom types and molecular environments of both atoms. The unique H(distance,anglescore) for the pair of atoms may be trained using machine learning algorithms. For example, H(distance anglescore) may equal $\vec{W} \cdot \vec{F}$, where $(x_1, x_2, x_3, \ldots, x_n)$ is the feature vector $\vec{F}$ for the correct pairwise interaction (i.e., the distance and angle for the pair of atoms in the conformation to be predicted), $(y_1, y_2, y_3, \ldots, y_n)$ is the feature vector for the incorrect pairwise interaction, and weight vector $\vec{W} = (w_1, w_2, w_3, \ldots, w_n)$. The weight factor W may be obtained such that $(\Sigma_{i=1}^n w_i x_i - \Sigma_{i=1}^n w_i y_i) > 0$. This way, the feature vector with the highest $\vec{W} \rightarrow \vec{F}$ corresponds to the pairwise interaction that is most energy favorable. The pairwise interactions with higher energy scores are more likely to occur in reality.

In exemplary embodiments, a machine-learning algorithm may be used to train the weight vector $\vec{W}$. The training data may be obtained from real-world protein structure data, such as Protein Database (PDB) files from the Research Collaboratory for Structural Bioinformatics (RCSB). For example, correct feature vectors may be constructed for the conformations shown in the PDB files and additional, incorrect conformations may be constructed. A machine-learning algorithm, e.g., a linear regression process, may then be executed to search for the $\vec{W}$ satisfying the equation $(\Sigma_{i=1}^{n} w_i x_i - \Sigma_{i=1}^{n} w_i y_i) > 0$.

As explained above, the scoring function H(distance, anglescore) may be used to calculate a pairwise potential energy score of the interaction of both atoms. Then all interactions consisting of a certain atom may be summed to provide a single pairwise potential energy feature for that particular atom.

Table 2 provides a list of exemplary atom pair features that may comprise a feature vector of atom pair a,b. Typical atom pair features include the inter-atomic distance and the bonding factors between two atoms.

TABLE 2

| Pair feature | Description | Size |
| --- | --- | --- |
| Bond type | One hot vector of {Single, Double, Triple} or null. | 3 |
| Distance | Distance of this atom pair. | 1 |
| Same ring | Whether the atoms are in the same ring. | 1 |

As shown in exemplary Table 2, in certain embodiments, a value indicating whether the bond between atom pair a and b is a single, double, or triple bond may be entered. A value indicating the distance between atoms a and b may also be entered. An indication that the two atoms are part of the same ring may also be entered.

Again, the dense feature vectors for the atoms and atom pairs of the ligand disclosed above are merely examples of information that may be provided to the system. One of ordinary skill in the art would understand suitable molecule description information to provide as quantized input to the system based at least on this disclosure.

Through this quantization process, the ligand may be represented by the quantized data. In an exemplary embodiment, the ligand may be represented by an unordered set of atom features $(A_a, A_b, \ldots A_n)$ and atom pair features $(P_{a,b}, P_{a,c}, \ldots P_{n-1,n})$.

Convolution Module

Figure 2:
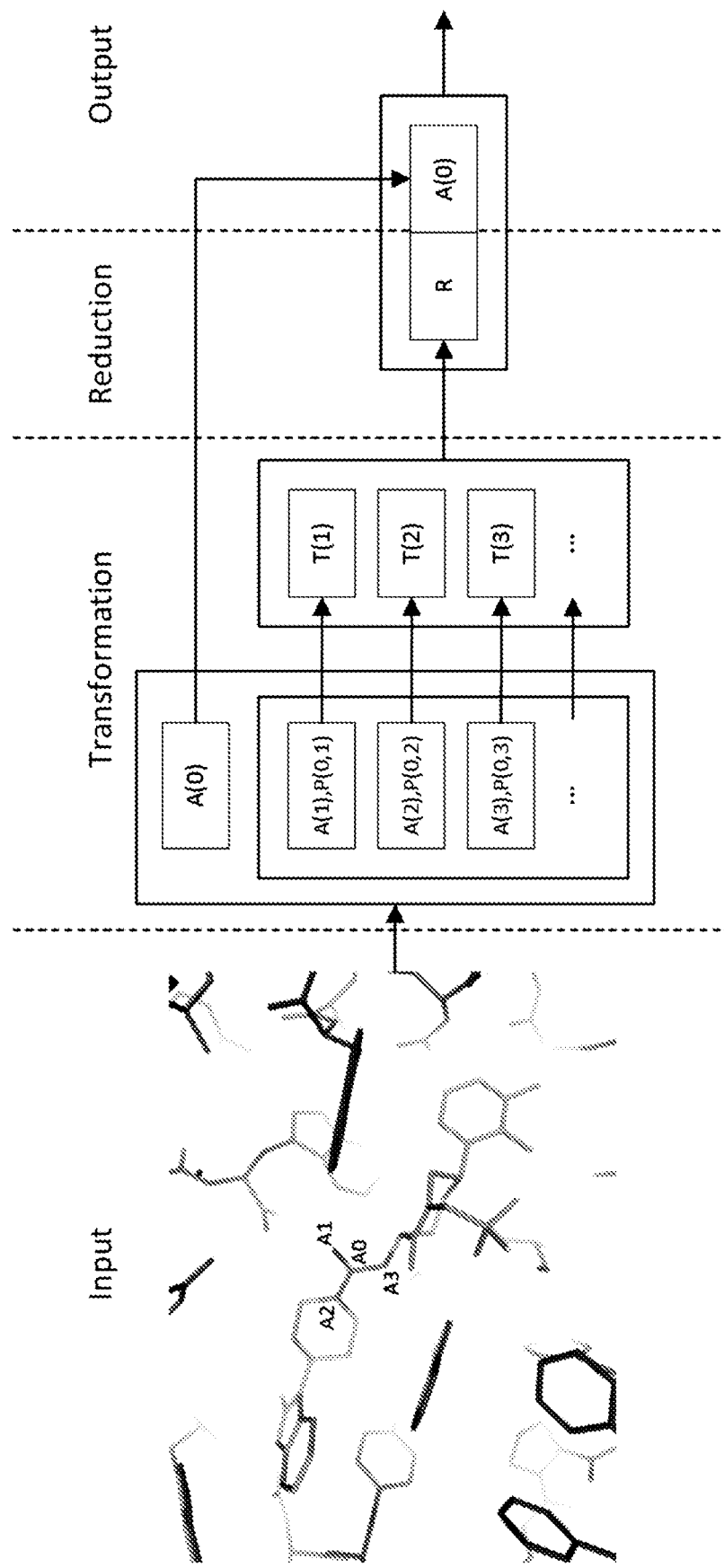
FIG. 2 is a flowchart of an example of a convolution filter structure according to one embodiment.

An exemplary embodiment of the convolution module is depicted in FIG. 2. In one embodiment, the inputs of this module are the dense feature vectors of the atoms and atom pairs, for example, as described above. In the convolution module, the feature vector of each atom is updated by first transforming the features of its neighbor atoms and atom pairs, then reducing the potentially variable sized feature vectors to a single feature vector by using a commutative reducing operator. In this embodiment, atom pair features are never changed throughout the process.

In this exemplary embodiment, the way the feature map is updated for each atom is the same, and they are formulated with shared weights. Unlike the convolutional operation in conventional convolutional neural networks (CNN), the convolution filter connections are dynamic instead of fixed.

The inputs to the convolution module are the initial dense feature vectors for each atom of the ligand, and the outputs of the convolution module are revised dense feature vectors for each atom of the ligand. Thus, the inputs and outputs of convolution module have the same number of dense feature vectors. Therefore, an arbitrary number of this module can be stacked. For example, as shown in FIG. 1, two convolution modules are stacked. In FIG. 1, the first convolution module, the central atom is in red, and the light blue highlights indicate concerned neighbor atoms. Information about the red atoms affects the dense atom vectors for that atom and its neighbor atoms. By stacking a second convolution layer, the information from the first convolution may be taken into account for atoms further away from the initial red central atoms. The purple highlights in the second stacked convolution module indicate the information flow area from previous convolution step. As seen with deep convolutional neural networks, more deep module stacking enables more complex structures of the molecule to be learned.

FIG. 2 shows an exemplary embodiment of the computation flow of a convolution filter. Important aspects of the filter are the transformation and reduction operators. In the transformation step, feature maps of neighbors of an atom are transformed by a feed-forward linear sub-network. For a neighbor atom b of current atom a, the input feature vector is the concatenation of atom feature $A_b$ and the atom pair feature $P_{a,b}$. The input is transformed through one fully connected layer and a non-linearity f:

$$T_{a,b}^k = f(W^k(\text{Concat}\{A_b^k, P_{a,b}\}) + B^k)$$

Figure 3:
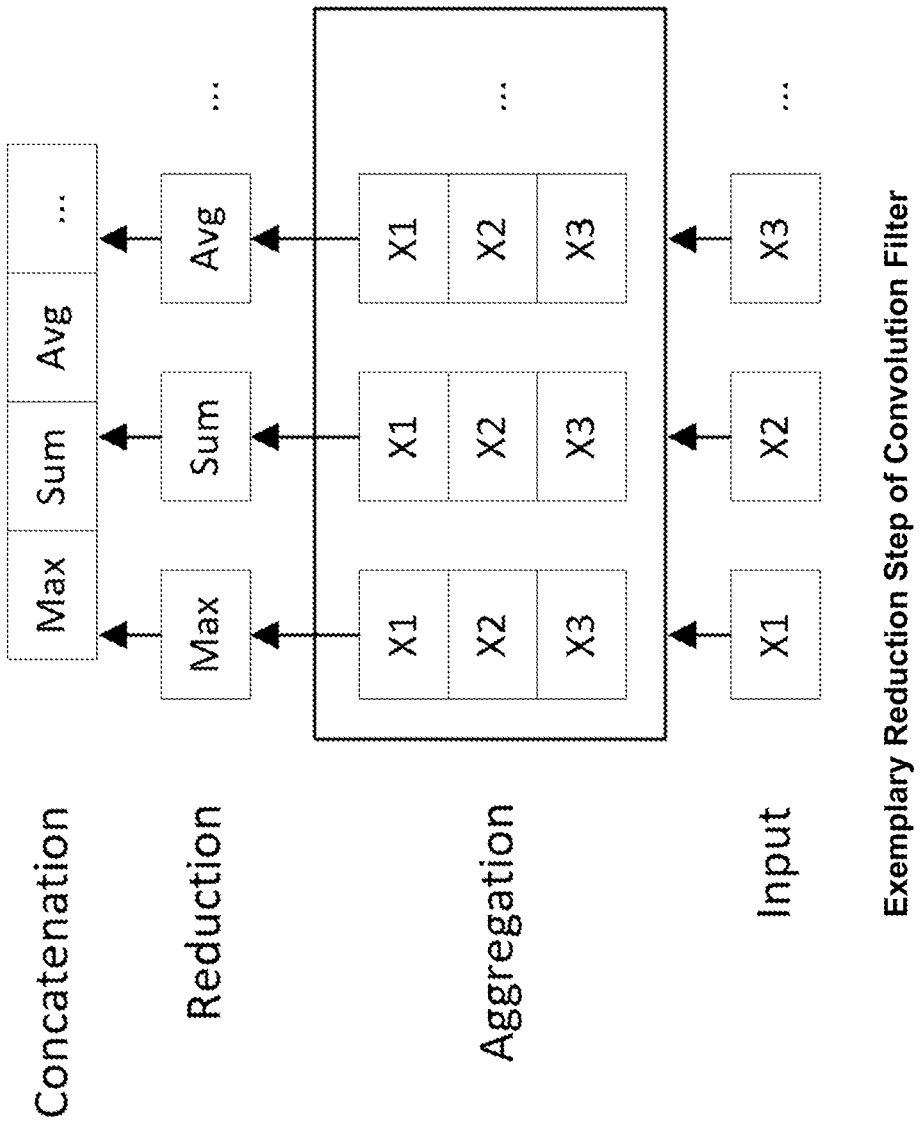
FIG. 3 is a flowchart of an example of a reduction step in the convolution filter according to one embodiment.

After each neighbor atom of a is transformed, these feature maps are then aggregated and reduced to a single feature map. In this process, a commutative reduction function is used to keep the order-invariant nature of input feature maps. A typical example of such a function is the element-wise sum function, which for input vectors $(X_1, X_2, \ldots X_3)$, the output vector Y is defined as: $Y_j = \Sigma_i^n X_{ij}$ In an exemplary embodiment, such as that shown in FIG. 3, a reduction module is constructed to improve model quality, in which multiple kinds of reduction operations are performed simultaneously and their outputs are combined. The reduction module may use the following exemplary equation: $R_a^k = \text{Concat}\{\text{Max}\{X_a^k\}, \text{Sum}\{X_a^k\}, \text{Avg}\{X_a^k\}\}$, where $X_a^k = \{T_{a,b}^k | b \in \text{neighbor}(a)\}$ The reduced feature map is then combined with the input feature map of atom a (FIG. 2) to produce the final output. This enables the model to obtain feature maps from different convolution levels more easily and is easier to optimize. The feature maps may be directly concatenated like: $A_a^{k+1} = \text{Concat}\{A_a^k, R_a^k\}$. Or the feature maps may be combined using a ResNet-like addictive combination: $A_a^{k+1} = A_a^k + R_a^k$. (He, 2016).

After the feature maps are obtained, they may be transformed into a feasibility score of the likelihood of the ligand binding to the pocket. The resulted score function is named the reranking score. Crystal structures (for example from RCSB) may be used to train the rerankings score. A binary classification model may be trained directly, or a regression model may be trained if such experimental data (Kd, Ki, etc) is added.

Docking: Anchor and Grow Operations

Based on the lock and key hypothesis, to determine the conformation of a ligand to a target, the possible key and possible lock shapes must be identified.

Determining the possible ligand conformations (key shapes) can be considered a sampling problem. That is, there is an essentially infinite variety of shapes that a ligand can make as each minute change of angle may be considered a different conformation. For practical reasons, this infinite set of options must be narrowed to a manageable group of samples that represent the likely shapes the ligand may take.

In the exemplary OrbitalDock system, ligand flexibility is limited to only dihedral angles, which is sufficient for a large number of cases. In order to prepare for the anchor and grow algorithm to provide fully formed conformation shapes (described below), the ligand (FIG. 4A) is split into small bricks which are connected via rotatable bonds (FIG. 4B). Bricks themselves are singular structures which cannot be modified.

Single bonds allow a dihedral angle to be rotated around the bond, as shown in FIG. 5a. Double and triple bonds limits dihedral angles to two discrete situations: 0 degree and 180 degrees, as shown in FIG. 2b.

In this way, the infinite set of conformations is narrowed to those that can be formed by the bricks and dihedral angles that make up the ligand.

To determine the locations and shapes of binding sites of the target (the lock shape(s)), a ridge and valley detection algorithm may be used. The binding site is then represented as a set of points which roughly depicts the shape of the binding site. This enables a more sophisticated strategy and heuristics to be applied, for example, the anchor and grow procedure described below. An example of binding site preparation is shown in FIG. 6a, while a cleaner result by clustering the pocket points into a smaller set is shown in FIG. 6b.

After the binding site has been identified, an anchor and grow strategy may be used for the docking algorithm. A visualization of the whole process is shown in FIGS. 7a-e.

Figure 8:
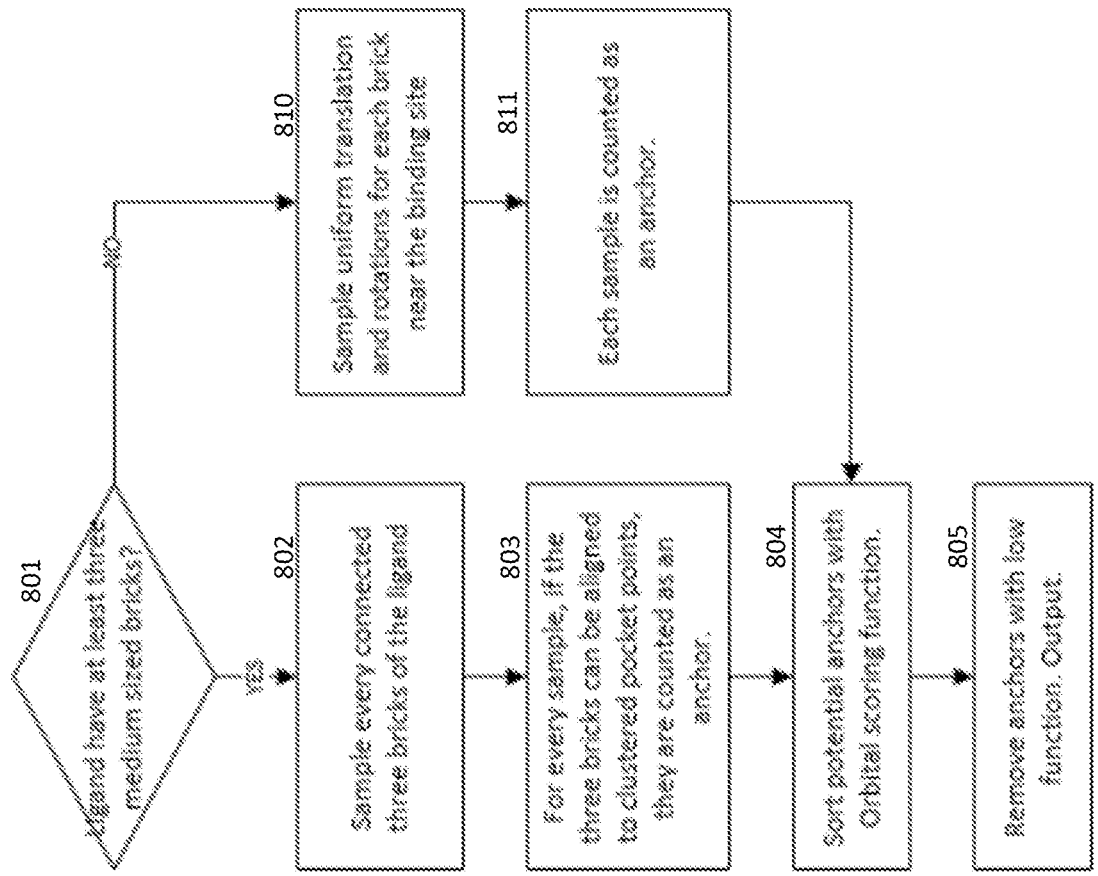
FIG. 8 is a flowchart of an example of an anchor algorithm, according to certain exemplary embodiments.

As shown in FIG. 7a, the anchor step places the first brick into the requested binding site to initiate the growing process. The details of the exemplary anchoring algorithm are shown in FIG. 8. The method of FIG. 8 may be executed by a processor. At step 801, the components of the ligand are analyzed to determine if the ligand comprises at least three medium-sized bricks. If a ligand does not have at least three medium sized bricks (step 801), then each brick is considered a sample and is translated and rotated around the binding site (step 810). Each sample is considered an anchor (step 811), and steps 804 and 805 proceed on each anchor.

If the ligand has three or more medium sized bricks, then in step 802 each connected three bricks is identified as a sample to be tested as an anchor for the ligand. For each three-brick sample, an attempt is made to align the three bricks into the clustered pocket points of the target (step 803). If the three-brick sample can be aligned to the clustered pocket points, it is counted as an anchor (step 803). If the three-brick sample cannot be clustered to a pocket point, it is discarded as a potential anchor and the next three-brick sample is tested (not shown). All potential anchors are sorted using a scoring function that correlates to the likelihood for the anchor to have that conformation in the real world (step 804).

In an exemplary embodiment, a scoring function is applied to sort the anchors (step 804). For example, if $(x_1, x_2, x_3, \ldots, x_n)$ is the feature vector $\vec{F}$ for the correct ligand conformation (i.e., the conformation to be predicted) and $(y_1, y_2, y_3, \ldots, y_n)$ is the feature vector for the incorrect ligand conformation, a weight vector $\vec{W}=(w_1, w_2, w_3, \ldots, w_n)$ may be obtained such that $(\Sigma_{i=1}^{n}w_i x_i - \Sigma_{i=1}^{n}w_i y_i) > 0$. This way, the feature vector with the highest $\vec{W} \cdot \vec{F}$ corresponds to the ligand conformation that is most energy favorable. The conformations with higher energy scores are more likely to occur in reality. Anchors with low scores are discarded and the remaining anchors are output to serve as the starting point for the grow algorithm (step 805).

In exemplary embodiments, a machine-learning algorithm may be used to train the weight vector $\vec{W}$. The training data may be obtained from real-world protein structure data, such as Protein Database (PDB) files from the Research Collaboratory for Structural Bioinformatics (RCSB). For example, correct feature vectors may be constructed for the conformations shown in the PDB files and additional, incorrect conformations may be constructed. A machine-learning algorithm, e.g., a linear regression process, may then be executed to search for the $\vec{W}$ satisfying the equation $(\Sigma_{i=1}^{n}w_i x_i - \Sigma_{i=1}^{n}w_i y_i) > 0$.

Figure 15:
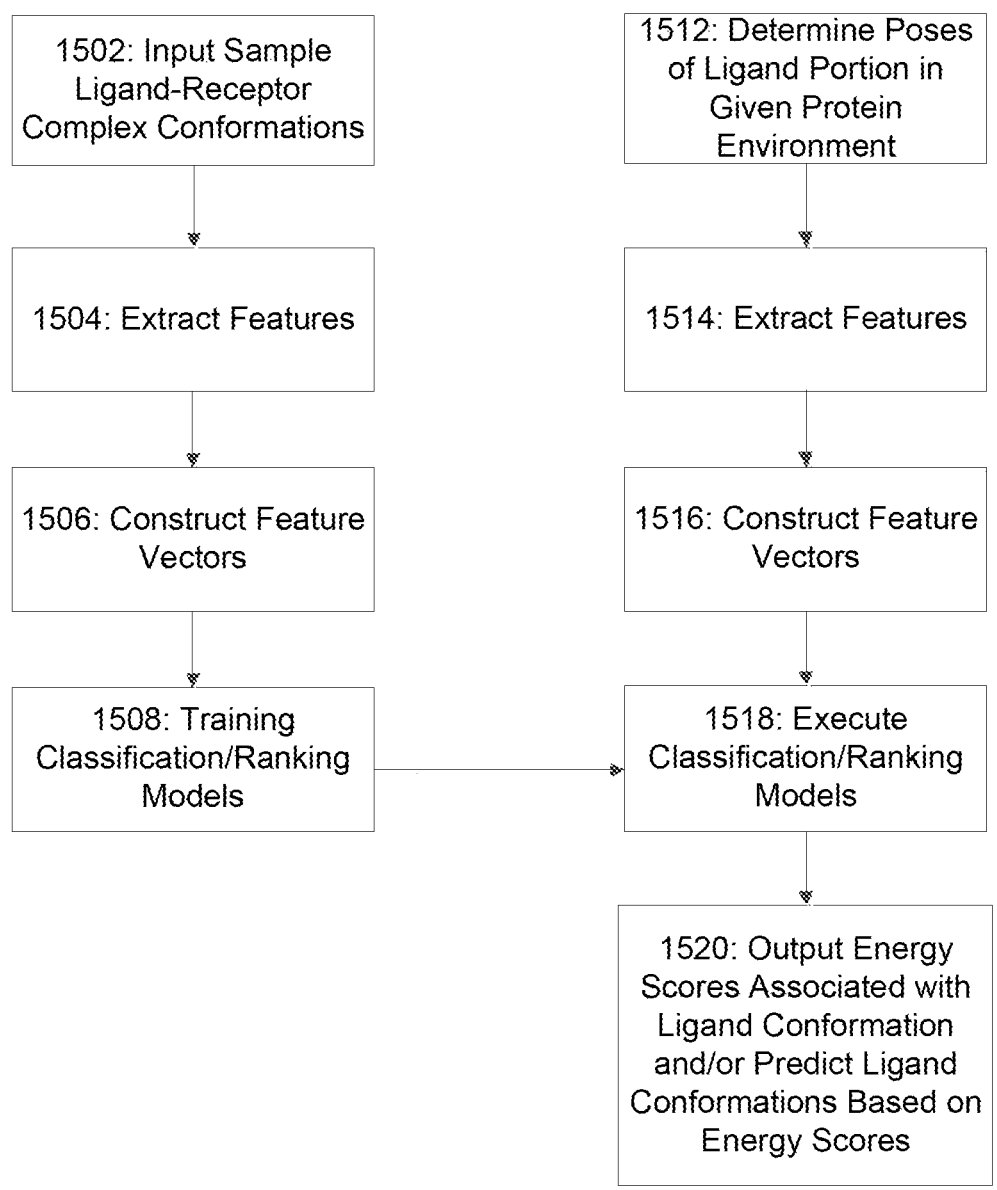
FIG. 15 provides a flowchart of an example of a method for predicting the conformation of ligand or portion of a ligand, according to an exemplary embodiment.

FIG. 15 is a flowchart of a method 1500 for predicting the conformation of a ligand, including the preferred anchor portions, according to an exemplary embodiment. For example, method 1500 may be executed by a processor. Referring to FIG. 15, steps 1502-1508 describe the training process for searching for the weight vector $\vec{W}$. Specifically, in step 1502, the processor obtains the training data. The processor may obtain correct ligand conformations based on ligand-receptor complexes in PDB files. The processor may also generate incorrect conformations used for the training. In step 1504, the processor extracts the features related to each conformation. In step 1506, the processor uses the extracted features to construct a feature vector for each conformation. In step 1508, the processor trains a classification model or a ranking model to search for the weight vector $\vec{W}$.

With continued reference to FIG. 15, Steps 1512-1520 describe the process of predicting an unknown conformation using the weight vector $\vec{W}$. Specifically, in step 1512, the processor determines the poses of the ligand or ligand portion in a given protein environment. Data regarding the protein environment may be extracted from a PDB file and include the conformations and sequences of other amino acids surrounding the ligand or ligand portion to be predicted.

In step 1514, the processor extracts the features associated with the poses of the ligand or portion of the ligand to be predicted. In step 1516, the processor uses the extracted features to construct the feature vector associated with each conformation of the ligand or portion of the ligand. For example, if the ligand conformation library contains 18 poses for the ligand or portion of the ligand, the processor needs to construct 18 feature vectors. In step 1518, the processor uses the classification model or ranking model trained in steps 1502-1508 to calculate the energy scores of the conformations. In step 1520, the processor outputs the energy scores. The conformations with higher energy scores are more appropriate for ligand. For example, the conformations of the sampled anchors for a particular ligand with the higher energy scores are more appropriate to act as anchors. Moreover, the processor may predict the conformations of the ligand, or portion of the ligand, based on the energy scores associated with the conformations. For example, the processor may compute the likelihood for each conformation to occur in the real world. For another example, the processor may determine the statistical average of the conformation based on the energy score.

Method 1500 uses the feature vectors and weight vectors to construct implicit energy terms and use a machine-learning algorithm to derive the correct energy scoring functions. This way, method 1500 ties the energy of a portion of a ligand with the conformation of the ligand portion, and avoids artificial construction of energy terms. Thus, method 1500 can accurately predict the ligand or ligand portion conformations.

The grow step of OrbitalDock iteratively extends the previously prepared anchor to fill the requested binding site, as shown in FIGS. 7*b-e*. Each grow step may grow single or multiple bricks from unlinked rotatable bonds in the current anchor. A uniform sampling of dihedral angles is also performed in merging bricks. Since a large number of conformations may be generated at each grow step, the entire growing procedure may be wrapped with a beam search to reduce the exponential search space to a linear space.

Figure 9:
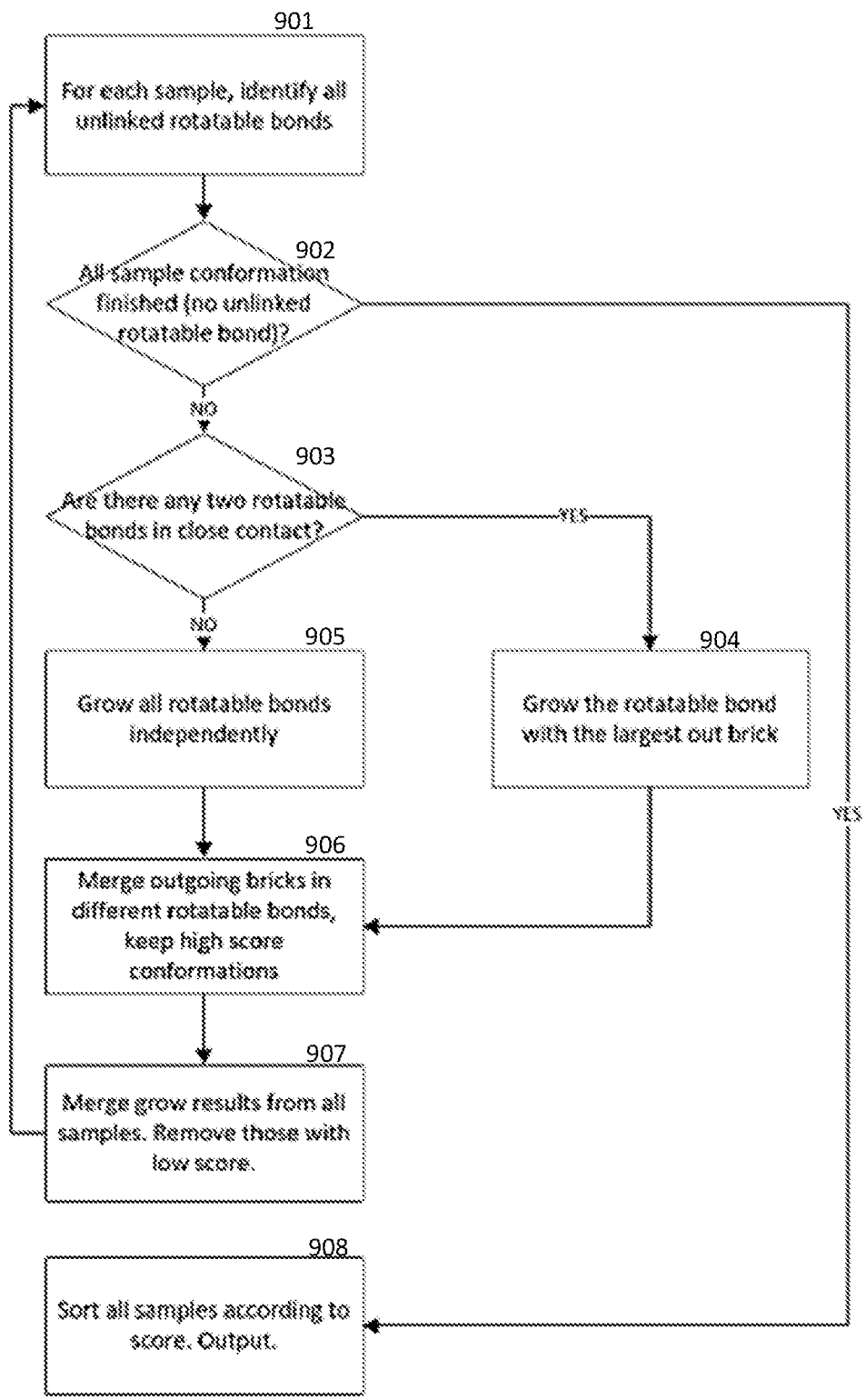
FIG. 9 is a flowchart of an example of a grow algorithm, according to certain exemplary embodiments.

FIG. 9 provides detailed steps of the exemplary grow algorithm. The method of FIG. 9 may be executed by a processor. At step 901, for each anchor sample that is output in step 805, all unlinked rotatable bonds are identified. These samples are used as a basis for the following sampling process. If no unlinked rotatable bonds exist, then the sample conformations are considered finished (step 902, yes), and the method proceeds to step 908. If unlinked rotatable bonds exist, then the sample conformations are not finished (step 902, no). If there are two rotatable bonds in close contact (step 903, yes), then the rotatable bond with the largest outbrick is grown (step 904). If there are not two rotatable bonds in close contact (step 903, no), then all rotatable bonds are grown independently (step 905). As a part of the grow step (step 904 or 905), the newly added outgoing bricks are rotated around the rotatable bonds and the scores for the various possible conformations are calculated. At step 906, independent grow conformations in step 904 and step 905 are combined and those conformations with the highest scores for each sample are kept. Step 903-906 handles a single sample in current sampled conformations. At step 907, the grow results from step 906 for all samples are merged, and those samples with low scores are removed. Then the process returns to step 901 to determine if current sampled conformations have any more unlinked rotatable bonds to grow. If there are no unlinked rotatable bonds left and the conformation sampling process is finished (step 902, yes), then the sampled conformations are sorted according to their respective scores and output in step 908.

After the anchor and grow process is finished, the conformations with highest score are outputted as the docking results. A reranking procedure may be applied in this step. The outputted conformations may be ranked according to another reranking score (described above).

Dynamic Batching Algorithm

Most neural network models use stochastic gradient descent or one of its variants for optimization. Mini-batched inputs are generally favored instead of feeding individual instances one by one in order to reduce computation overhead during forward and backward passes. This is because each neural network operation call has a fixed overhead. Batching many similar operations into one large operation can reduce such overhead and reserve more time for actual computation. In most conventional neural network models, the computation graph can be statically determined and is the same for all input data. In these cases, mini-batching can be easily implemented to speed up training and inference.

The disclosed ranking neural network, however, depends on the structure of input ligand-target complexes, hence has highly dynamic computation graphs. Conventional neural network implementations fail to support batching on such model because the computation graph is heterogeneous for each input.

To overcome this issue, a novel and efficient dynamic batching algorithm is proposed. This algorithm analyzes the computation graph for each input batch dynamically and merges compatible neural network operations without affecting the computation correctness.

Additionally, unlike conventional neural network implementations, which only support batching at instance level, the dynamic batching algorithm supports batching neural network operations in intra- and inter-instances. This is important for efficiently running heterogeneous convolution layers.

Figure 10:
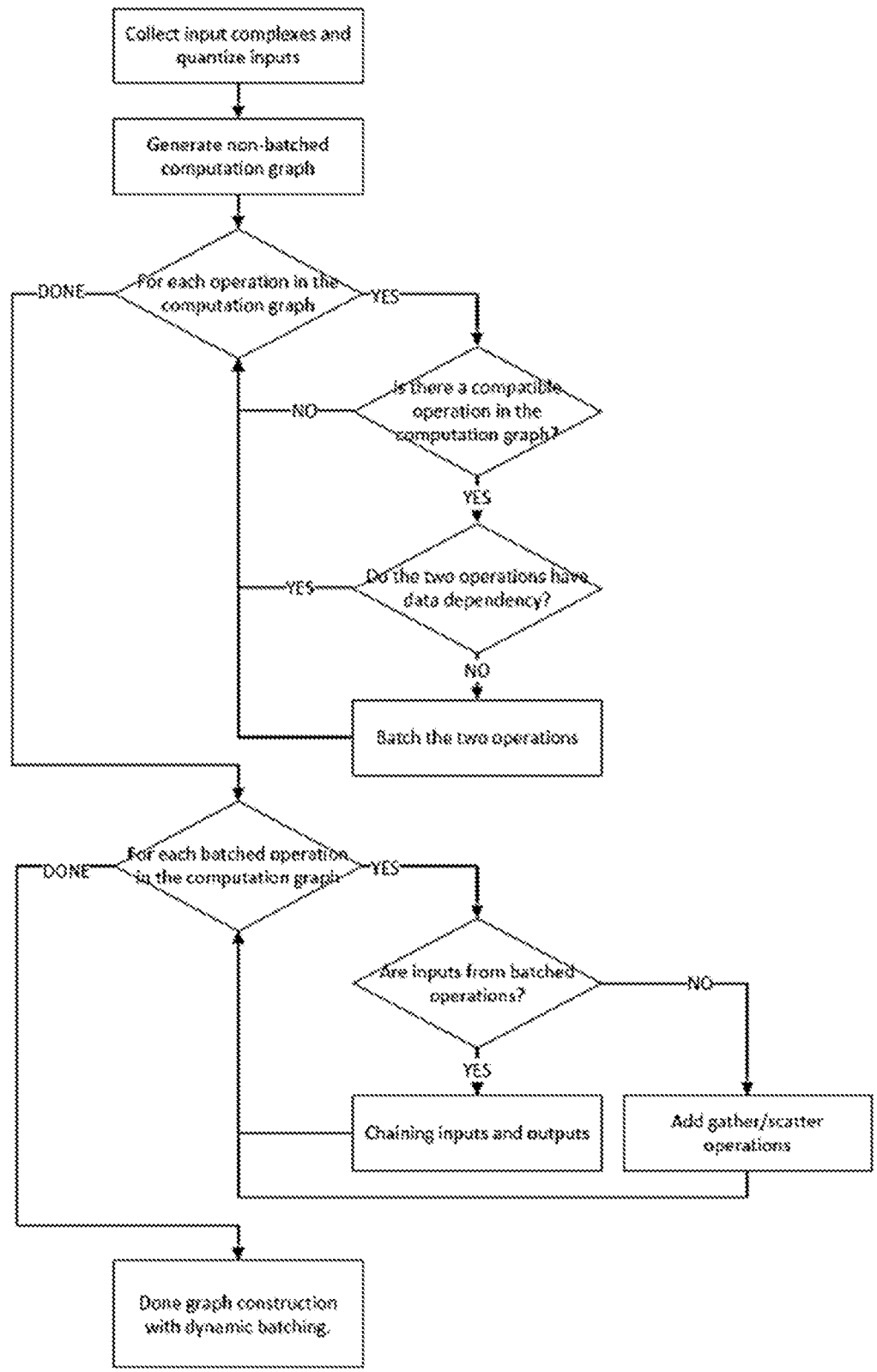
FIG. 10 is a flowchart of an example of a dynamic batching algorithm, according to certain exemplary embodiments.

The detailed dynamic batching algorithm is shown in FIG. 10. The algorithm can be divided into three portions: computation graph initialization (steps 1001-1002), batching analysis (steps 1003-1006), and gather/scatter operation generation (steps 1007-1010).

During initialization, the input ligand-target complexes and quantized inputs are collected (step 1001), and an initial un-batched computation graph for each input instance is generated (step 1002). The computation graph is a directed acyclic graph (DAG).

In the batching analysis portion, the structure of the computation graph is examined so that compatible operations without data dependency are batched. In particular, each operation in the computation graph is examined (step 1003) to determine if there are compatible operations in the computation graph (step 1004), and if so, if the two operations have data dependency (step 1005). If there are compatible operations that do not have the same data dependency, then the two operations can be batched (step 1006). These steps are repeated until all operations on the computation graph have been reviewed, at which point, the batching analysis portion is complete, and the process continues to the gather/scatter operation generation portion of the process.

In the gather/scatter operation generation portion, gather and scatter operations are generated for the inputs and outputs of the batched operation(s). In particular, each batched operation is analyzed (step 1007) to determine if there are inputs which are outputted from a batched operation, with exactly matched data shape (step 1008). If so, the corresponding output from the batched operation is directly chained to this input such that no gather and scatter operations are needed for this input (step 1009). If not, gather/scatter operations are added to the computation graph. This optimization ensures that scatter-gather operation pairs between two batched operations can be eliminated. The output of this process is a final graph construction with dynamic batching (step 1010).

Example 1: Neural Network Model Training and Evaluation

Consistent with the disclosed embodiments, the deep neural network based ranking model was trained using a two-class classification setting. High resolution X-ray crystallography structures of receptor-ligand complexes deposited in the Research Collaboratory for Structural Bioinformatics (RCSB) protein database (PDB) were taken as true examples. The co-crystalized ligand in X-ray structures were re-docked using the docking protocol described above.

That is, the exemplary OrbitalDock system was tasked with determining the most likely conformations for ligand-target complexes based on the separate ligand and target data, using the docking methods described above (ridge and valley detection of binding sites; anchor and grow methods of ligand samples).

Sampling results with a high deviation from the crystal structure were labeled as negative examples. Therefore, the sampling space for negative examples was essentially infinite.

In this training data generation process, 5681 positive examples and 25421 negative examples were obtained.

AUC and AUPR rates were used to evaluate the classification accuracy. In practice, recall rate is more important than precision rate since drug discovery is comparable to an information retrieval task. To model the actual usage scenario, a precision@K like metric was used. Suppose there are K positive examples in the test dataset, the precision@K metric calculates the ratio of correctly identified positive examples in the top K ranked outputs, sorted by descending order of score.

The performance of the exemplary OrbitalDock system was tested using multiple settings. Models were named as convolution parameter n and atom pair parameter m ("convn-apm"). Parameter n is the number of convolution layers in the model. Parameter m is the maximum graph distance to be considered in the atom pair features. m=1 corresponds to cases where only directly bonded atoms were considered, whereas m=∞ was used when all atoms in the ligand were considered. The binary cross entropy loss and AdaM optimizer (Kingma, 2014) were also used to train the neural network. The results are shown below in Table 3.

TABLE 3

Neural Network Model Evaluation

| Model | Test AUC | Test AUPR | P@K/2 | P@K |
|---|---|---|---|---|
| conv1-ap2 | 0.992875 | 0.827927 | 0.998603 | 0.992486 |
| conv2-ap2 | 0.993405 | 0.824541 | 1 | 0.930866 |
| conv3-ap2 | 0.995006 | 0.827099 | 0.997207 | 0.937151 |
| conv4-ap2 | 0.994958 | 0.824724 | 0.997207 | 0.937849 |
| conv5-ap2 | 0.994458 | 0.826399 | 0.997207 | 0.931564 |
| conv3-ap1 | 0.993621 | 0.826085 | 1 | 0.928771 |
| conv3-ap2 | 0.995006 | 0.827099 | 0.997207 | 0.937151 |
| conv3-ap3 | 0.994036 | 0.826568 | 0.997207 | 0.929469 |
| conv3-ap∞ | 0.99294 | 0.828929 | 0.99581 | 0.918296 |
| conv4-ap1 | 0.993435 | 0.826 | 1 | 0.922486 |
| conv4-ap2 | 0.994958 | 0.824724 | 0.997207 | 0.937849 |

With fixed maximum graph distance and different number of convolution layers, the performance is significantly improved as the number of layers increases at first. Perhaps due to limited size of training set, the choice of convolution layer number beyond 5 does not provide additional improvement, but harm the performance on the contrary. The optimal maximum graph distance was determined as 2, by testing the combinatory performance with fixed number of convolution layers (3 or 4) and varied maximum graph distance (ranging 1 to 3, or ∞). A distance limit greater than 2 may introduce great difficulties in training, as the pooling layer may throw away too much information and gradient.

Example 2: Redocking Evaluation

Docking tasks have applications in following three stages of the drug discovery process: (1) to predict the binding conformation of a known active ligand; (2) to enable a virtual screening to identify new active ligands, which is aimed at discovering new leading drugs; and (3) to predict the binding affinities of untested compounds to a target site (Leach, 2006).

Of these three stages, the first stage provides a readily testable scenario for comparing known docking platforms to the disclosed system and methods. The RCSB PDB's high quality co-crystal structures provide a good testing set for the first stage to compare different docking platforms, and the large-scale and reliable data allows for an unbiased comparison different methods for the latter two tasks are still lacking.

To compare the disclosed systems against current platforms, a redocking evaluation was performed which systematically compare how close the top predicted poses or conformations for each platform deviated from the genuine X-ray conformation. The goal for this study was to compare the baseline performances of different docking platforms, hence, different programs were run with default settings to eliminate any potential influence from the user. Of the approximately 10,000 co-crystal structures available, 1,441 PDBs were chosen based on the following criteria: (1) the chosen PDBs' resolution must be better than 2.4 Å; (2) the chosen PDBs showed different ligands (redundant or duplicative ligands were removed so that all 1,441 PDBs were unique); (3) the chosen ligands have ready-to-dock 3D structures in PubChem (Kim, 2015); and (4) the chosen ligands have no more than 10 rotatable bonds.

The following docking platforms were tested:

The exemplary OrbitalDock system, which embodies the disclosed systems and methods.

Glide, which is a widely used docking tool that offers molecular docking and virtual screening. XP (extra precision), SP (standard precision) and HTVS (high-throughput virtual screening) are the three options offered by Glide.

UCSF DOCK version 6.7, which supports two docking modes, flexible and rigid. In flexible mode the ligand dihedral angles are flexible, while in rigid mode the ligand dihedral angles are fixed, that is ligand is generally only rigidly transformed.

AutoDock Vina, which is a tool for molecular docking and virtual screening, developed by Molecular Graphics Lab at The Scripps Research Institute.

Rosetta, which provides various tools, such as predicting protein-protein interaction and protein—small molecule docking.

Each of the platforms were tasked with re-docking the ligand-receptor complexes for the selected 1,441 PDBs. To evaluate the results, the average Root-Mean-Square-Deviation (RMSD) and average shape RMSD for the top 1 and top 5 poses were then calculated. RMSD is a direct, symmetric method for evaluating docking results. It is defined using the following formula:

$$RMSD(a_i, b_i) = \sqrt{\frac{1}{N}\sum_{i=1}^{N}(a_i - b_i)^2}$$

where $a_i$ is the set of points of ground truth ligand, and $b_i$ is the set of points of redocked ligand. In the calculation of the RMSD criteria, the most important part is to find the atom correspondence between the two ligand conformations. Because the ligand may have identical symmetric substructures, there may be more than one appropriate correspondence.

Because the ground truth conformation of a ligand is obtained by modeling ligand atoms into the electron density map calculated from x-ray diffraction pattern, sometimes the modeling may introduce errors when the local density map quality is not good enough. For this reason, a shape-based RMSD criterion was also used. The shape-based RMSD only compared the density relationship between two conformations. Instead of finding an atom correspondence between two ligands, only the nearest atoms between ground truth conformation ligand and sampled conformation ligand were used for RMSD calculation.

The calculated RMSD and average shape RMSD for the top 1 and top 5 poses are shown in FIG. 11. The results of the disclosed methods, as used in the exemplary Orbital-Dock system, were qualitatively more superior than other docking platforms with an average top 1 predicted poses of ~1.8 Å per atom deviation from the true X-ray position as compared to ~2.8 Å with the Glide extra precision mode (XP); ~2.6-3.2 Å with the UCSF dock best performance flexible mode; ~2.7 Å with AutoDock Vina, and ~2.7 Å with Rosetta dock. Improvement of this scale has not been seen in the over-20 years since the docking problem first arose.

Rerank Score to Identify Pharmacophors

To identify potential pharmacophors or molecular features of ligands important in the binding process, a rerank score is disclosed. The rerank score is indicative of the likelihood of drug pocket binding to portion of a ligand.

To create the rerank score, an "omitting" function is used to probe which portion of the ligand (typically a substructure of a ligand) was critical for the binding reaction. Each chemical compound is modeled using an undirected graph model which considers each bond as an edge and each bi-connected component as a block. The omitting rerank score is constant within each block of the given ligand.

The omitting score for each block is calculated by first removing that block from the ligand. When the removed block was at the end of a ligand, then one continuous portion of the ligand is left. When the removed block is in the middle of the ligand, then two separate portions of the ligand are left (with the block missing from the middle). The largest remaining portion of the ligand is then used to calculate a partial rerank score with the drug binding pocket. That is, the largest remaining ligand portion is re-docked to the target and a score is calculated for that portion. This omitting rerank score is then assigned to the atoms in the omitted block.

In an exemplary embodiment, a high omitting score indicates that the corresponding atoms or the block are not critical for the binding, as the remaining portions excluding this block retains a relatively high likelihood of binding to the receptor. Conversely, a low omitting score indicates that the corresponding atoms or block are critical for binding, as the remaining portions excluding the block retains a relatively low likelihood of binding to the receptor.

Example 3: Identifying Pharmacophors

In the exemplary OrbitalDock system, the rerank score ranges from 0 and 1. After the omitting scores were determined for all the atoms in a ligand, the heat map of the omitting score for the ligands were color coded from blue (close to 0, low omitting score, likely critical for binding) to red (close to 1, high omitting score, likely not critical for binding).

FIGS. 12a-c provide heat maps showing the omitting scores for three different ligands. FIG. 12a provides the omitting score heat map for the von Hippel-Lindau (VHL) ligase ligand (with the Hypoxia Inducible Factor (HIF) Alpha Subunit as target) (PDB 4W9H). FIG. 12b provides the omitting score heat map for the Human Estrogen Receptor Alpha (ERα) ligand (with 4-Hydroxytamoxifen as target) (PDB 3ERT). FIG. 12c provides the omitting score heat map for the Human PPARdelta ligand (with specific agonist 1 as target) (PDB 5U3Q).

Interestingly, the hydroxyl-proline motifs (e.g., in FIG. 12a) were colored blue by the exemplary OrbitalDock system, which is indicative of the pharmacophore role for VHL E3 ligase ligands. In fact, experimental evidence has suggested that in order for effective recognition by VHL E3 ligase, the native substrate protein HIF2 peptide needs to be processed by proline hydroxylase to create a hydroxyl-proline motif (Rogers, 2010). As a result, multiple VHL inhibitors have been designed centered on the hydroxyl-proline moiety (Gómez-Bombarelli, 2016).

Similarly, the heat map plot of the omitting score of ligand in an ERα case as shown in FIG. 12b identified only one of the three seemingly equal aromatic rings of the 4-OH tamoxifen ligand as being particularly important to binding. The hydroxylation at the C4 position of the very same ring element was shown to increase the binding affinity of ~100 fold compared to the original tamoxifen mother compound (Blair, 2000).

Additionally, the heat map plot of the omit score for a PPARδ (an important target related to metabolic disease such as obesity) ligand shown in FIG. 12c is also supported by recent medicinal chemistry efforts.

Figure 13:
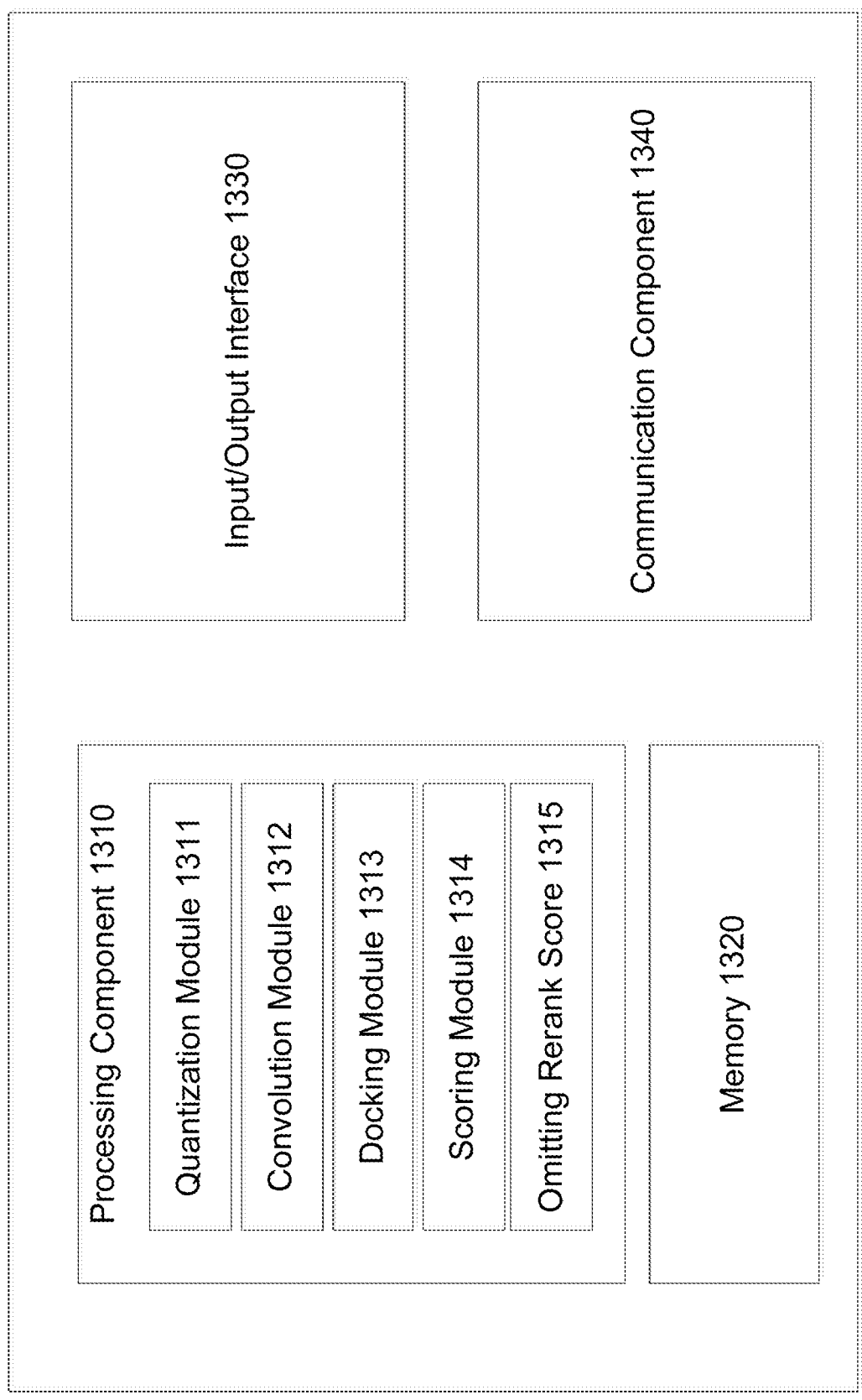
FIG. 13 provides a block diagram of an example of a device for predicting ligand docking, according to an exemplary embodiment.

FIG. 13 is a block diagram of a device 1300 for predicting ligand conformations, according to an exemplary embodiment. For example, device 1300 may be a desktop, a laptop, a server, a server cluster consisting of a plurality of servers, a cloud computing service center, etc. Referring to FIG. 13, device 1300 may include one or more of a processing component 1310, a memory 1320, an input/out (I/O) interface 1330, and a communication component 1340.

Processing component 1310 may control overall operations of device 1300. For example, processing component 1310 may include one or more processors that execute instructions to perform all or part of the steps in the following described methods. In particular, processing component 1310 may include a quantization module 1311 configured to receive, determine, and/or calculate the quantified information for an input, such as the dense feature vectors $A_a$, $P_{(a,b)}$. Processing component 2210 may include a convolution module 1312 for performing the convolution operations that, for example, transform the dense feature vectors and assigns weights to them so that various conformations can be tested and ranked. Processing component 2210 may include a docking module 1313 that, for example, determines the shape and location of target binding sites and uses the anchor and grow method to develop conformations for ligands. Processing component 2210 may include a scoring module 1314 that, for example, provides scores and/or ranks the potential ligand conformations. Processing component 2210 may also include an omitting rerank score module 1315 that, for example, can identify potential pharmacophors using an omitting function.

Further, processing component 1310 may include one or more modules (not shown) which facilitate the interaction between processing component 1310 and other components. For instance, processing component 1310 may include an I/O module to facilitate the interaction between I/O interface and processing component 1310.

Processing component 1310 may include one or more application specific integrated circuits (ASICs), digital signal processors (DSPs), digital signal processing devices (DSPDs), programmable logic devices (PLDs), field programmable gate arrays (FPGAs), controllers, micro-controllers, microprocessors, or other electronic components, for performing all or part of the steps in the above-described methods.

Memory 1320 is configured to store various types of data and/or instructions to support the operation of device 1300. Memory 1320 may include a non-transitory computer-readable storage medium including instructions for applications or methods operated on device 1300, executable by the one or more processors of device 1300. For example, the non-transitory computer-readable storage medium may be a read-only memory (ROM), a random access memory (RAM), a CD-ROM, a magnetic tape, a memory chip (or integrated circuit), a hard disc, a floppy disc, an optical data storage device, or the like.

I/O interface 1330 provides an interface between the processing component 1310 and peripheral interface modules, such as input and output devices of device 1300. I/O interface 1330 may employ communication protocols/methods such as audio, analog, digital, serial bus, universal serial bus (USB), infrared, PS/2, BNC, coaxial, RF antennas, Bluetooth, etc. For example, I/O interface 1330 may receive user commands from the input devices and send the user commands to processing command 1310 for further processing.

Communication component 1340 is configured to facilitate communication, wired or wirelessly, between device 1300 and other devices, such as devices connected to the Internet. Communication component 1340 can access a wireless network based on one or more communication standards, such as Wi-Fi, LTE, 2G, 3G, 4G, 5G, etc. In some embodiments, communication component 1340 may be implemented based on a radio frequency identification (RFID) technology, an infrared data association (IrDA) technology, an ultra-wideband (UWB) technology, a Bluetooth (BT) technology, or other technologies. For example, communication component 1340 may access the PDB files via the Internet and/or send the prediction results to a user.

This application is intended to cover any variations, uses, or adaptations of the present disclosure following the general principles thereof and including such departures from the present disclosure as come within known or customary practice in the art. Other embodiments of the present disclosure will be apparent to those skilled in the art from consideration of the specification and practice of the present disclosure. It is intended that the specification and examples be considered as exemplary only, with a true scope and spirit of the invention being indicated by the following claims.

In particular, variations of the disclosed methods will be apparent to those of ordinary skill in the art, who may rearrange and/or reorder the steps, and add and/or omit certain steps without departing from the spirit of the disclosed embodiments. Non-dependent steps may be performed in any order, or in parallel.

REFERENCES

Allen, William J, Trent E Balius, Sudipto Mukherjee, Scott R Brozell, Demetri T Moustakas, P Therese Lang, David A Case, Irwin D Kuntz, and Robert C Rizzo. Dock Impact of new features and current docking performance. Journal of computational chemistry, 36(15):1132-1156, 2015.

Ballester, P. J. and J. B. Mitchell, A machine learning approach to predicting protein-ligand binding affinity with applications to molecular docking. Bioinformatics, 2010. 26(9): p. 1169-75.

Berman, Helen M., John Westbrook, Zukang Feng, Gary Gilliland, Talapady N Bhat, Helge Weissig, Ilya N Shindyalov, and Philip E Bourne. The protein data bank. Nucleic acids research, 28(1):235-242, 2000.

Blair, R. M., et al., The estrogen receptor relative binding affinities of 188 natural and xenochemicals: structural diversity of ligands. Toxicol Sci, 2000. 54(1): p. 138-53.

Buckley, D. L., et al., Targeting the von Hippel-Lindau E3 ubiquitin ligase using small molecules to disrupt the VHL/HIF-1alpha interaction. J Am Chem Soc, 2012. 134(10): p. 4465-8.

DeLuca, Samuel, Karen Khar, and Jens Meiler. Fully flexible docking of medium sized ligand libraries with rosettaligand. PLOS one, 10(7):e0132508, 2015. Doman, T N., et al., Molecular docking and high-throughput screening for novel inhibitors of protein tyrosine phosphatase-1B. J Med Chem, 2002. 45(11): p. 2213-21.

Duvenaud, David K, Dougal Maclaurin, Jorge Iparraguirre, Rafael Bombarell, Timothy Hirzel, Alán Aspuru-Guzik, and Ryan P Adams. Convolutional networks on graphs for learning molecular fingerprints. In Advances in neural information processing systems, pages 2224-2232, 2015.

Ewing, T. J. A. and I. D. Kuntz, Critical evaluation of search algorithms for automated molecular docking and database screening. Journal of Computational Chemistry, 1997. 18(9): p. 1175-1189.

Friesner, R. A., et al., Extra Precision Glide: Docking and Scoring Incorporating a Model of Hydrophobic Enclosure for Protein-Ligand Complexes. Journal of Medicinal Chemistry, 2006. 49(21): p. 6177-6196.

Friesner, R. A., et al., Glide: A New Approach for Rapid, Accurate Docking and Scoring. 1 Method and Assessment of Docking Accuracy. Journal of Medicinal Chemistry, 2004. 47(7): p. 1739-1749.

Gómez-Bombarelli, Rafael, David Duvenaud, José Miguel Hernández-Lobato, Jorge Aguilera-Iparraguirre, Timothy D Hirzel, Ryan P Adams, and Alán Aspuru-Guzik. Automatic chemical design using a data-driven continuous representation of molecules. arXiv preprint arXiv: 1610.02415, 2016.

Halgren, T. A., et al., Glide: a new approach for rapid, accurate docking and scoring. 2. Enrichment factors in database screening. J Med Chem, 2004. 47(7): p. 1750-9.

Halgren, T. A., et al., Glide: A New Approach for Rapid, Accurate Docking and Scoring. 2. Enrichment Factors in Database Screening. Journal of Medicinal Chemistry, 2004. 47(7): p. 1750-1759.

Hartman, G. D., et al., Non-peptide fibrinogen receptor antagonists. 1. Discovery and design of exosite inhibitors. J Med Chem, 1992. 35(24): p. 4640-2.

He, Kaiming, Xiangyu Zhang, Shaoqing Ren, and Jian Sun, Deep residual learning for image recognition. In Proceedings of the IEEE Conference on Computer Vision and Pattern Recognition, pages 770-778, 2016.

Huang, N., et al., Molecular mechanics methods for predicting protein-ligand binding. Phys Chem Chem Phys, 2006. 8(44): p. 5166-77, Kearnes, Steven, Kevin McCloskey, Marc Berndl, Vijay Pande, and Patrick Riley. Molecular graph convolutions: moving beyond fingerprints. Journal of computer-aided molecular design, 30(8):595-608, 2016.

Kim, Sunghwan, Paul A Thiessen, Evan E Bolton, Jie Chen, Gang Eu, Asta Gindulyte, Lianyi Han, Jane He, Siqian He, Benjamin A Shoemaker, et al. Pubchem substance and compound databases. Nucleic acids research, page gkv951, 2015.

Kingma, Diederik P. and Jimmy Ba. Adam: A method for stochastic optimization, CoRR, abs/1412.6980, 2014.

Leach, A. R., B. K. Shoichet, and C. E. Peishoff, Prediction of protein-ligand interactions. Docking and scoring: successes and gaps. J Med Chem, 2006. 49(20): p. 5851-5.

Leach, A. R., Molecular modelling: principles and applications. Pearson education, 2001, LeCun, Y., Y. Bengio, and G. Hinton, Deep learning. Nature, 2015. 521(7553): p. 436-444.

MacKerell Jr A D, Bashford D, Bellott M, et al. All-atom empirical potential for molecular modeling and dynamics studies of proteins, The journal of physical chemistry B (1998) 102(18): 3586-3616.

Meiler, J. and D. Baker, ROSETTALIGAND: Protein—small molecule docking with full side-chain flexibility. Proteins: Structure, Function, and Bioinformatics, 2006. 65(3): p. 538-548.

Mnih, V., et al., Human-level control through deep reinforcement learning. Nature, 2015. 518(7540): p. 529-533.

Rogers, David and Mathew Hahn. Extended-connectivity fingerprints. Journal of chemical information and modeling, 50(5):742-754, 2010, Segler, Marwin H S, Thierry Kogej, Christian Tyrchan, and Mark P Waller. Generating focused molecule libraries for drug discovery with recurrent neural networks. arXiv preprint arXiv:1701.01329, 2017, Shoichet, B. K., I. D. Kuntz, and D. L. Bodian, Molecular docking using shape descriptors. Journal of Computational Chemistry, 1992. 13(3): p. 380-397, Szegedy, Christian, Wei Liu, Yangqing Jia, Pierre Sermanet, Scott Reed, Dragomir Anguelov, Dumitru Erhan, Vincent Vanhoucke, and Andrew Rabinovich. Going deeper with convolutions. In Proceedings of the IEEE Conference on Computer Vision and Pattern Recognition, pages 1-9, 2015.

Talele, T. T., S. A. Khedkar, and A. C. Rigby, Successful applications of computer aided drug discovery: moving drugs from concept to the clinic. Curr Top Med Chem, 2010. 10(1): p. 127-41.

Trott, O. and A. J. Olson, AutoDock Vina: Improving the speed and accuracy of docking with a new scoring function, efficient optimization, and multithreading. Journal of Computational Chemistry, 2010. 31(2): p. 455-461.

Vijayakrishnan, R., Structure-based drug design and modern medicine. J Postgrad Med, 2009. 55(4): p. 301-4, Wang, L., et al., Accurate and Reliable Prediction of Relative Ligand Binding Potency in Prospective Drug Discovery by Way of a Modern Free-Energy Calculation Protocol and Force Field. Journal of the American Chemical Society, 2015. 137(7): p. 2695-2703.

Chyuan-Chuan Wu, Thomas J Baiga, Michael Downes, James J La Clair, Annette R Atkins, Stephane B Richard, Weiwei Fan, Theresa A Stockley-Noel, Marianne E Bowman, Joseph P Noel, et al. Structural basis for specific ligation of the peroxisome proliferator-activated receptor. Proceedings of the National Academy of Sciences, 114 (13):E2563-E2570, 2017.

Yu, F., et al., HIF-1alpha binding to VHL is regulated by stimulus-sensitive proline hydroxylation. Proc Natl Acad Sci USA, 2001. 98(17): p. 9630-5.

Zwanzig, R. W., High-Temperature Equation of State by a Perturbation Method. I. Nonpolar Gases. The Journal of Chemical Physics, 1954. 22(8): p. 1420-1426.

What is claimed is:

1. A computer-implemented method for predicting a conformation of a ligand docked into a protein, the method comprising:
   determining one or more poses of the ligand, the poses being representative conformations of the ligand;
   extracting features associated with the poses of the ligand;
   constructing, based on the extracted features, feature vectors associated with the poses of the ligand;
   determining, using a neural network, scores associated with the poses, wherein the determining of the scores associated with the poses comprises at least one convolution of the constructed feature vectors associated with the poses, the convolution of each feature vector comprising a transformation operator and a reduction operator; and
   determining a proper conformation for the docked ligand based on the scores.

2. The method of claim 1, wherein determining one or more poses of the ligand comprises:
   dividing the ligand into two or more sections;
   anchoring a first section of the two or more ligand sections to a location of the protein;
   adding at least one subsequent section of the two or more ligand sections to the first section to form a growing ligand; and
   continuing adding subsequent sections to the growing ligand until the ligand is complete.

3. The method of claim 1, wherein the extracted features comprise features of a first atom and features of the interaction between the first atom and a second atom.

4. The method of claim any of claim 3, wherein the features of the first atom comprise one or more of an atom type, a radius of the atom, a number of rings in which the atom is included, a size of the ring in which the atom is included, whether the first atom is part of an aromatic ring, or the pairwise potential of the first atom.

5. The method of claim 4, wherein the pairwise potential of the first atom comprises the sum of the pairwise atom potentials between the first atom and atoms of the protein.

6. The method of claim 3, wherein the features of the interaction between the first atom and the second atom comprise one or more of a bond type, a distance between the first and second atoms, or whether the first and second atoms are in the same ring.

7. The method of claim 1, wherein the constructed feature vectors comprise a dense feature vector for each atom of the ligand, wherein each dense feature vector including the features of an atom and features of the interaction between that atom and another atom.

8. The method of claim 1, wherein determining, using a neural network, scores associated with the poses comprises two convolutions of the feature vectors associated with the poses of the ligand.

9. The method of claim 1, wherein the transformation operator comprises transforming the feature vectors of neighbor atoms of an atom of interest by a feed-forward linear sub-network.

10. The method of claim 9, wherein the reduction operator comprises:
    aggregating the transformed feature vectors of neighbor atoms of the atom of interest;
    applying a commutative reduction function to the aggregated transformed feature vectors of neighbor atoms of an atom of interest to produce a reduced feature map for the atom of interest.

11. The method of claim 9, wherein the convolution process further comprises an optimization operator that combines the initial feature vector of an atom of interest with the feature vector output after the application of the transformation operator and reduction operator, resulting in a final feature vector for the atom of interest.

12. The method of claim 1, wherein
the feature vector of each neighbor atom comprises a dense feature vector,
the dense feature vector comprises an atom feature vector for the neighbor atom and an atom pair feature vector for the neighbor atom and the atom of interest, and
the dense feature vector is input into the transformation operator as a concatenation of the atom feature vector and the atom pair feature vector, and
the input is transformed through a fully connected layer and a non-linearity function.

13. The method of claim 1, wherein determining, using a neural network, scores associated the poses comprises applying a scoring function to the feature vectors of the atoms of the ligand for each pose.

14. The method of claim 13, wherein the scoring function is a weighted scoring function that applies a weighted vector to the feature vectors of the atoms of the ligand for each pose, wherein the weighted vector is determined by a machine-learning algorithm.

15. The method of claim 14, wherein the machine-learning algorithm for determining the weight vector is trained on real-world protein structure data.

16. The method of claim 15, wherein the training of the machine-learning algorithm comprises determining a weight vector $\vec{W}=(w_1, w_2, w_3, \ldots, w_n)$ for the real-world protein structure data, where, when the feature vector for the correct ligand conformation equals $(x_1, x_2, x_3, \ldots, x_n)$ and the feature vector for an incorrect ligand conformation is $(y_1, y_2, y_3, \ldots, y_n)$, $\vec{W}$ satisfies the equation $(\Sigma_{i=1}^{n} w_i x_i - \Sigma_{i=1}^{n} w_i y_i) > 0$.

17. The method of claim 1, wherein determining a proper conformation for the docked ligand based on the scores comprises ranking the scores associated with the ligand poses.

18. The method of claim 1, wherein determining one or more poses of the ligand comprises:
dividing the ligand into two or more sections;
anchoring a first section of the two or more ligand sections to a first location of the protein;
anchoring a second section of the two or more ligand sections to a second location of the protein, wherein the second location of the protein may be the same or different than the first location of the protein;
extracting features associated with the anchored first section of the ligand and features associated with the anchored second section of the ligand;
constructing, based on the extracted features, feature vectors associated with the anchored first section of the ligand and feature vectors associated with the anchored second section of the ligand;
determining, using a neural network, scores associated with the anchored first section and anchored second section; and
determining a proper anchor for the docked ligand based on the scores.

19. The method of claim 1, wherein the method further comprises generating a graphical representation of the determined proper conformation for the docked ligand.

20. A computer-implemented method for predicting a conformation of a ligand docked into a protein, the method comprising:
dividing the ligand into two or more sections;
anchoring a first section of the two or more ligand sections to a location of the protein;
extracting features associated with the anchored first section;
constructing, based on the extracted features, feature vectors associated with the anchored first section;
determining, using a neural network, a score associated with the anchored first section, wherein the determining of the score comprises at least one convolution of the constructed feature vectors, the convolution of each feature vector comprising a transformation operator and a reduction operator; and
determining a proper conformation for the docked ligand based on the score.

21. A computer-implemented method for predicting an anchor section of a ligand docked into a protein, the method comprising:
dividing the ligand into two or more sections;
anchoring a first section of the two or more ligand sections to a first location of the protein;
anchoring a second section of the two or more ligand sections to a second location of the protein, wherein the second location of the protein may be the same or different than the first location of the protein;
extracting features associated with the anchored first section of the ligand and features associated with the anchored second section of the ligand;
constructing, based on the extracted features, feature vectors associated with the anchored first section of the ligand and feature vectors associated with the anchored second section of the ligand;
determining, using a neural network, scores associated with the anchored first section and anchored second section, wherein the determining of the scores comprises at least one convolution of the constructed feature vectors, the convolution of each feature vector comprising a transformation operator and a reduction operator; and
determining a proper anchor for the docked ligand based on the scores.

22. The method of claim 21, wherein the method further comprises generating a graphical representation of the anchor section of the ligand.

23. A computer-implemented method for predicting a conformation of a potential growing ligand section docked into a protein, the method comprising:
dividing the ligand into a plurality of sections;
creating a first growing ligand section by:
anchoring a first section of the plurality of sections to a first location of the protein; and
adding a second section of the plurality of sections to the first section in a first conformation;
creating a second growing ligand section by:
anchoring a first section of the plurality of sections to a first location of the protein; and
adding a second section of the plurality of sections to the first section in a second conformation;
extracting features associated with the first growing ligand section and features associated with the second growing ligand section;

constructing, based on the extracted features, feature vectors associated with the first growing ligand section and feature vectors associated with the second growing ligand section;

determining, using a neural network, scores associated with the first growing ligand section and the second growing ligand section, wherein the determining of the scores comprises at least one convolution of the constructed feature vectors, the convolution of each feature vector comprising a transformation operator and a reduction operator; and determining a potential growing ligand section for the docked ligand based on the scores.

24. The method of claim 23, wherein the method further comprises generating a graphical representation of the potential growing ligand section.

* * * * *